United States Patent
Gardner et al.

(10) Patent No.: US 10,842,471 B2
(45) Date of Patent: Nov. 24, 2020

(54) BIOPSY COLLECTOR WITH IDENTIFIER

(71) Applicant: SNPSHOT TRUSTEE LIMITED, Auckland (NZ)

(72) Inventors: Michael Stuart Gardner, Auckland (NZ); Roy Victor Bladen, Auckland (NZ)

(73) Assignee: SNPSHOT TRUSTEE LIMITED, Auckland (NZ)

(*) Notice: Subject to any disclaimer, the term of this patent is extended or adjusted under 35 U.S.C. 154(b) by 712 days.

(21) Appl. No.: 15/030,203

(22) PCT Filed: Oct. 17, 2014

(86) PCT No.: PCT/IB2014/065395
§ 371 (c)(1),
(2) Date: Apr. 18, 2016

(87) PCT Pub. No.: WO2015/056227
PCT Pub. Date: Apr. 23, 2015

(65) Prior Publication Data
US 2016/0249891 A1  Sep. 1, 2016

(30) Foreign Application Priority Data

Oct. 18, 2013 (NZ) .................................. 616807
Jun. 5, 2014 (NZ) .................................. 625902
Jun. 5, 2014 (NZ) .................................. 625904

(51) Int. Cl.
*A61B 10/02* (2006.01)
*A01K 11/00* (2006.01)
(Continued)

(52) U.S. Cl.
CPC .......... *A61B 10/0266* (2013.01); *A01K 11/00* (2013.01); *A01K 11/003* (2013.01);
(Continued)

(58) Field of Classification Search
CPC ................ A01K 11/003; A01K 11/002; A61B 10/0096; A61B 10/0266
See application file for complete search history.

(56) References Cited

U.S. PATENT DOCUMENTS 4,976,925 A   12/1990   Porcher
6,235,036 B1   5/2001   Gardner et al.
(Continued)

FOREIGN PATENT DOCUMENTS

AU   2009329486   11/2014
CN   1275894   12/2000
(Continued)

OTHER PUBLICATIONS

Office Action from the US Patent and Trademark Office for U.S. Appl. No. 14/896,325 dated Sep. 27, 2018 (18 pages).
(Continued)

*Primary Examiner* — Patrick Fernandes
(74) *Attorney, Agent, or Firm* — Michael Best & Friedrich LLP

(57) ABSTRACT

A sample collector to take and hold a biopsy sample from an organism upon being driven by an actuator into the organism, the collector comprising a punch that includes a cutter with a cutting edge formed at a cutting end of the punch to remove and retain a biopsy sample, and a unique identifier on or in the collector, the identifier being machine or human readable at the time of use of the collector to take the sample.

12 Claims, 22 Drawing Sheets

(51) Int. Cl.
*A61B 10/00* (2006.01)
*A61B 90/00* (2016.01)

(52) U.S. Cl.
CPC ........ *A01K 11/006* (2013.01); *A61B 10/0096* (2013.01); *A61B 10/0283* (2013.01); *A61B 2010/0208* (2013.01); *A61B 2010/0225* (2013.01); *A61B 2090/081* (2016.02); *A61B 2503/40* (2013.01); *A61B 2562/08* (2013.01)

(56) References Cited

U.S. PATENT DOCUMENTS

| | | |
|---|---|---|
| 6,631,650 B1 | 10/2003 | Espinosa |
| 6,659,338 B1 | 12/2003 | Dittmann |
| 6,696,923 B2 | 2/2004 | Ishii et al. |
| 6,753,759 B2 | 6/2004 | Stegmaier et al. |
| 6,947,866 B2 | 9/2005 | Staab |
| 6,968,639 B2 | 11/2005 | Destoumieux |
| 7,235,055 B2 | 6/2007 | Pfistershammer |
| 7,467,760 B2 | 12/2008 | Schieli et al. |
| 7,528,725 B2 | 5/2009 | Stewart |
| 7,764,177 B2 | 7/2010 | Stewart |
| 7,764,181 B2 | 7/2010 | Stewart et al. |
| 7,791,409 B2 | 9/2010 | Arrigo |
| 7,936,272 B2 | 5/2011 | Stewart |
| 8,070,757 B2 | 12/2011 | Eadie |
| 8,159,291 B2 | 4/2012 | Arrigo |
| 8,361,416 B2 | 1/2013 | Berner |
| 8,581,705 B2 | 11/2013 | Stewart |
| 8,668,655 B2 | 3/2014 | Destoumieux |
| 8,763,287 B2 | 7/2014 | Hilpert |
| 8,854,188 B2 | 10/2014 | Stewart |
| 9,554,557 B2 | 1/2017 | Nehis |
| 10,299,768 B2 | 5/2019 | Gardner et al. |
| 2002/0120216 A1 | 8/2002 | Fritz et al. |
| 2004/0103567 A1 | 6/2004 | Destoumieux |
| 2004/0167429 A1 | 8/2004 | Roshdieh |
| 2004/0167430 A1 | 8/2004 | Roshdieh |
| 2004/0232323 A1 | 11/2004 | Bosco et al. |
| 2005/0038355 A1 | 2/2005 | Gellman et al. |
| 2005/0228310 A1 | 10/2005 | Pfistershammer |
| 2005/0256425 A1 | 11/2005 | Prusiner |
| 2005/0272057 A1 | 12/2005 | Abrahamsen |
| 2007/0239067 A1 | 10/2007 | Hibner |
| 2008/0064983 A1 | 3/2008 | Stromberg |
| 2008/0170967 A1 | 7/2008 | Itoh |
| 2008/0227662 A1 | 9/2008 | Stromberg |
| 2008/0228105 A1 | 9/2008 | Howell et al. |
| 2009/0270878 A1 | 8/2009 | Eadie |
| 2010/0016758 A1 | 1/2010 | Hilpert |
| 2010/0084364 A1 | 4/2010 | Martin |
| 2010/0160830 A1 | 6/2010 | Schmiedl |
| 2010/0168616 A1 | 7/2010 | Schraga et al. |
| 2010/0210011 A1 | 8/2010 | Hilpert |
| 2010/0286556 A1 | 11/2010 | Decaluwe et al. |
| 2010/0291662 A1 | 11/2010 | Berner |
| 2011/0127177 A1 | 6/2011 | Hostettler |
| 2011/0269228 A1 | 11/2011 | Decaluwe |
| 2011/0295148 A1* | 12/2011 | Destoumieux ....... A01K 11/003 600/564 |
| 2012/0010526 A1 | 1/2012 | Hilpert |
| 2012/0016263 A1 | 1/2012 | Hilpert |
| 2013/0040358 A1 | 2/2013 | Woods |
| 2013/0204159 A1 | 8/2013 | Destoumieux |
| 2013/0211287 A1 | 8/2013 | Decaluwe |
| 2013/0211416 A1 | 8/2013 | Teychene |
| 2014/0034183 A1 | 2/2014 | Gross |
| 2014/0249449 A1 | 9/2014 | Hilpert |
| 2015/0112225 A1 | 4/2015 | Prow et al. |
| 2015/0226646 A1 | 8/2015 | Lardi et al. |
| 2016/0007567 A1 | 1/2016 | Decaluwe et al. |

FOREIGN PATENT DOCUMENTS

| | | |
|---|---|---|
| CN | 102933157 | 2/2013 |
| CN | 103052313 | 4/2013 |
| DE | 19835014 | 8/1999 |
| DE | 20022647 | 1/2002 |
| EP | 0016236 | 10/1980 |
| EP | 982688 | 3/2000 |
| EP | 1014861 | 7/2000 |
| EP | 1060662 | 12/2000 |
| EP | 1318718 | 6/2003 |
| EP | 1781086 | 9/2007 |
| EP | 1920651 | 5/2008 |
| EP | 1809096 | 2/2009 |
| EP | 2066170 | 6/2009 |
| EP | 2068718 | 6/2009 |
| EP | 2160093 | 3/2010 |
| EP | 2168207 | 3/2010 |
| EP | 2249966 | 11/2010 |
| EP | 2265109 | 12/2010 |
| EP | 2307136 | 4/2011 |
| EP | 2355653 | 8/2011 |
| EP | 2378863 | 10/2011 |
| EP | 2384618 | 11/2011 |
| EP | 2384619 | 11/2011 |
| EP | 1718142 | 10/2012 |
| EP | 2579781 | 4/2013 |
| EP | 2579782 | 4/2013 |
| EP | 2597944 | 6/2013 |
| EP | 2736324 | 6/2014 |
| EP | 2770819 | 9/2014 |
| FR | 2939281 | 6/2010 |
| GB | 2358061 | 7/2001 |
| GB | 2482036 | 1/2012 |
| IN | 201200015 | 5/2012 |
| JP | 2006026227 | 2/2007 |
| JP | 2012511310 | 5/2012 |
| JP | 2012514201 | 6/2012 |
| JP | 2012526966 | 11/2012 |
| JP | 2013079859 | 5/2013 |
| NZ | 503521 | 12/2002 |
| NZ | 575341 | 1/2012 |
| NZ | 593039 | 12/2012 |
| NZ | 596853 | 2/2014 |
| NZ | 608927 | 11/2014 |
| SU | 946587 | 7/1982 |
| WO | 200051496 | 9/2000 |
| WO | 2001040762 | 6/2001 |
| WO | 2002023980 | 3/2002 |
| WO | 2002039810 | 5/2002 |
| WO | 2005101273 | 10/2005 |
| WO | 2006000869 | 1/2006 |
| WO | 2007013820 | 2/2007 |
| WO | 2008037802 | 4/2008 |
| WO | 2008040692 | 4/2008 |
| WO | 2008101497 | 8/2008 |
| WO | 2009008861 | 1/2009 |
| WO | 2009010658 | 1/2009 |
| WO | 2009046957 | 4/2009 |
| WO | 2009095178 | 8/2009 |
| WO | 2009120206 | 10/2009 |
| WO | 2009127541 | 10/2009 |
| WO | 2010012446 | 2/2010 |
| WO | 2010066475 | 6/2010 |
| WO | 2010070129 | 6/2010 |
| WO | 2010070130 | 6/2010 |
| WO | 2011044585 | 4/2011 |
| WO | 2011073359 | 6/2011 |
| WO | 2011154233 | 12/2011 |
| WO | 2011154510 | 12/2011 |
| WO | 2012013429 | 2/2012 |
| WO | 2013014034 | 1/2013 |
| WO | 2013060690 | 5/2013 |
| WO | 2013155557 | 10/2013 |
| WO | 2014153181 | 9/2014 |
| WO | 2015014461 | 2/2015 |
| WO | 2015158787 | 10/2015 |

(56) References Cited

FOREIGN PATENT DOCUMENTS

| WO | 2016016204 | 2/2016 |
|----|------------|--------|
| WO | 2016073754 | 5/2016 |

OTHER PUBLICATIONS

International Preliminary Report on Patentability for Application No. PCT/IB2014/065395 dated Sep. 2, 2015 (5 pages).
International Search Report for Application No. PCT/IB2014/065395 dated Feb. 10, 2015 (5 pages).
International Search Report for Application No. PCT/IB2014/065394 dated Feb. 9, 2015 (3 pages).
International Preliminary Report on Patentability for Application No. PCT/IB2014/065394 dated Feb. 3, 2016 (4 pages).
International Search Report for Application No. PCT/IB2014/065397 dated Feb. 26, 2015 (3 pages).
International Preliminary Report on Patentability for Application No. PCT/IB2014/065397 dated Feb. 3, 2016 (4 pages).
International Search Report for Application No. PCT/IB2014/065393 dated Feb. 3, 2015 (6 pages).
International Preliminary Report on Patentability for Application No. PCT/IB2014/065393 dated Feb. 3, 2016 (7 pages).
International Search Report for Application No. PCT/IB2014/065396 dated Feb. 19, 2015 (6 pages).
Written Opinion from the International Searching Authority for Application No. PCT/IB2014/065396 dated Feb. 19, 2015 (7 pages).
Office Action from the US Patent and Trademark Office for U.S. Appl. No. 14/896,322 dated Jun. 12, 2018 (13 pages).
Office Action from the US Patent and Trademark Office for U.S. Appl. No. 15/030,211 dated Nov. 20, 2018 (12 pages).
Office Action from the US Patent and Trademark Office for U.S. Appl. No. 14/896,322 dated Feb. 4, 2019 (13 pages).
Office Action issued from the United States Patent Office for related U.S. Appl. No. 15/030,205 dated Jul. 17, 2019 (7 pages).

\* cited by examiner

BIOPSY COLLECTOR WITH IDENTIFIER

CROSS-REFERENCE TO RELATED APPLICATIONS

This application is a national stage filing under 35 U.S.C. § 371 of International Application No. PCT/IB2014/065395, filed Oct. 17, 2014, which claims foreign priority to New Zealand Application No. 625904, filed Jun. 5, 2014, New Zealand Application No. 625902, filed Jun. 5, 2014, and New Zealand Application No. 616807, filed Oct. 18, 2013. The entire contents of all four applications are incorporated herein by reference.

FIELD OF THE INVENTION

The invention relates to a biopsy collector with identifier.

BACKGROUND OF THE INVENTION

To improve the tracking of livestock and to facilitate DNA testing, tissue samples may be collected from animals. A tissue sample may be taken from an animal at any time. The tissue sample is usually cut from an animal using a tissue sampling device and is placed in a storage container for laboratory analysis.

United States patent numbers US20110295148A1 and US20130204159A1 describe a tissue sampler in the shape of a clamp and comprising a pair of jaws that move toward each other. The sample taken be taken to a laboratory and analysed.

Tampering with the sample between the stages of collection and analysis can cause inaccuracies in the analysis records kept. There is hence a need to improve sample tracking and prevent tampering of samples to ensure accuracy of records.

It is an object of the present invention to provide a biopsy collector with identifier that goes at least some way toward overcoming the disadvantages as mentioned above and/or that will at least provide the public with a useful choice.

SUMMARY OF THE INVENTION

In a first aspect the present invention may broadly be said to be a sample collector to take and hold a biopsy sample from an organism upon being driven by an actuator into the organism, the collector comprising a punch that includes a cutter with a cutting edge formed at a cutting end of the punch to remove and retain a biopsy sample, and a unique identifier on or in the collector, the identifier being machine or human readable at the time of use of the collector to take the sample.

Preferably the unique identifier comprises an EID embedded in a body of the collector.

Preferably the EID is embedded in a body of the punch.

Preferably the sample collector includes a plunger mounted to the punch, actuable to eject the sample from the punch, the EID being embedded in a body of the plunger.

Preferably the sample collector includes features to engage with a vial or cover, to close in the sample, the vial or cover having its own unique identifier.

In a further aspect the present invention may broadly be said to be a set of sample collectors, each sample collector adapted to take and hold a biopsy sample from an organism upon being driven by an actuator into the organism and comprising a punch that includes a cutter with a cutting edge formed at a cutting end of the punch to remove and retain a biopsy sample, and an identifier on or in the collector, the identifier being machine or human readable at the time of use of the collector to take the sample; the sample collectors of the set all being identical except in respect of the identifier, the identifier of each sample collector being unique across the set of sample collectors.

Preferably the identifier comprises an EID embedded in a body of the collector.

Preferably the EID is embedded in a body of the punch.

Preferably a set of sample collectors include a plunger mounted to the punch, actuable to eject the sample from the punch, the EID being embedded in a body of the plunger.

In a further aspect the present invention may broadly be said to be a method of taking samples including:
a. presenting a sample collector to an actuation location of a tissue sampler, the sample collector being adapted to take and hold a biopsy sample from an organism upon being driven by an actuator into the organism, the collector comprising a punch that includes a cutter with a cutting edge formed at a cutting end of the punch to remove and retain a biopsy sample, and a unique identifier on or in the collector,
b. reading and storing the identity of the sample collector together with additional information including at least one of:
   i. an identity of a vial or cover connected or to be connected with the sample collector
   ii. an identity of an organism being sampled.

Preferably the applicator includes a reader to read an identity of a sample collector presented in the actuation location.

Preferably the identifier is an EID, and the reader reads the EID.

Preferably the reader also reads an EID located on or in the organism being sampled.

Preferably the collector comprising:
a punch that includes a cutter with a cutting edge formed at a cutting end of the punch to remove and retain a biopsy sample and a plunger retained to said punch in a manner to allow it to move relative said cutter to remove a cutter retained biopsy sample from the cutter.

Preferably the plunger is mounted to said punch.

Preferably the plunger is secured to said punch in a movable manner.

Preferably the plunger is not caused to be moved relative said punch by said actuator upon driving of the collector into the organism.

Preferably the collector is driven through said organism.

Preferably just the cutter is driven through said organism.

Preferably at least the cutting edge is pushed through a part of the organism to remove and retain a biopsy sample.

Preferably the plunger does not protrude out of said passage.

In a further aspect the present invention may broadly be said to be a sampler tool to cooperate with the collector as hereinbefore described, the tool comprising a body carrying a ram to drive the collector and able to be actuated to move along a path relative the body between a first position aligned to drive the collector from a primed position and push the cutter through part of an organism and a second position where said cutter has been so pushed through by said ram, to remove a sample from said organism, the tool also comprising an EID reader and preferably an EID read information storage device.

Preferably the tool includes a magazine receptacle, to hold a magazine containing a plurality of said collectors, the magazine receptacle allowing the magazine to move relative the tool so that each collector can be presented in a manner for being driven by said ram.

In a further aspect the present invention may broadly be said to be a sample retaining sample collector comprising a sample collector as hereinbefore described wherein a sample from an organism removed by said cutter is retained by said cutter and said plunger is in a position relative said punch able to move said sample from cutter.

Also herein described is a dispenser to dispenser a sample from a sample retaining sample collector as herein described the dispenser including a pusher able to move said plunger toward the cutting end of the punch to eject the sample from the cutter without the pusher directly contacting the sample.

Preferably the pusher only contacts the plunger.

Preferably the pusher does not contact the punch.

Preferably the magazine is the same as that from which the collectors were stored prior to sampling.

Also herein described is an assembly of a sample retaining sample collector as herein described and a storage container comprising a container body having an opening closed by a removable cap together defining a containment region, the cap including a passage into said containment region, sealed by said collector, said collector holding said sample in said containment region.

Also herein described is an assembly of a collectors and container as herein described having been assembled by a tool that comprising a body able to hold said collector and said container and carrying a ram to drive the collector from (a) a primed position, separated from said container by a part of the organism from which the sample is to be cut, through said part of said organism to (b) a second position where said collector has been driven through said part of said organism by said ram, to remove a sample from said organism, the second position lodging said collector at said passage with said container body.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The entire disclosures of all applications, patents and publications, cited above and below, if any, are hereby incorporated by reference.

"EID" as used herein means electronic identification. This refers to identification systems that provide remote communication of identity data from a tag to a reader. The remote communication may be by electromagnetic wave at radio frequency (as for example an RFID system), but may be by other means for means (for example sound or magnetic field). "EID tag" as used herein means an item that can communicate with a reader to return data to the reader regarding the identity of the device. The tag may be attached, included or embedded in an object or item to be identified. Presently the most readily available EID systems are RFID systems.

Any reference to prior art documents in this specification is not to be considered an admission that such prior art is widely known or forms part of the common general knowledge in the field.

BRIEF DESCRIPTION OF THE DRAWINGS

Preferred forms of the invention will now be described by way of example only and with reference to the accompanying drawings, in which:

FIG. 2b is a side view of the punch of FIG. 2a;

FIG. 2c is an end view showing the pushing end of the punch of FIG. 2a;

FIG. 2e is an end view showing the cutting end of the punch of FIG. 2a;

FIG. 3b is a side view of the body of FIG. 3a;

FIG. 3c is a cross-sectional side view of the body taken along line A-A of FIG. 3a;

FIG. 3d is an end view of the closed second end of the body of FIG. 3a;

DETAILED DESCRIPTION OF PREFERRED FORMS OF THE INVENTION

Reference will now be made to a collector for collecting a biopsy sample from an organism. The sample may be from plants or animals particularly, including pigs, goats, cattle, sheep, poultry, and fish. It is preferably a tissue sample taken from the ear of an animal. In use, the collector may optionally be used together with a storage container so that together the collector and container can collect and store a biopsy sample for later analysis. The use of a storage container with the collector may not be required in certain manners of use of the collector.

The invention particularly relates to inclusion of a unique identifier in or on a collector. In the preferred form the unique identifier is a machine readable electronic ID tag (EID), such as an RFID tag.

The collector includes a cutter for cutting a tissue sample. The collector is thrust into or through the tissue to be sampled, and a sample of the tissue is retained within the cutter. The collector may then be capped by a cap or container, to enclose and protect the sample. An example collector will be described in more detail, but the adaptation of the present invention can be used in other tissue sample collecting devices.

The process of collecting the sample is facilitated by a tissue sampler which includes a mechanism to drive a selected sample collector through or into tissue to be sampled, and to cap the collector in the same action. An example tissue sampler will be described in more detail, but tissue sample collectors incorporating the present invention can be used with other tissue samplers.

Figure 1A:
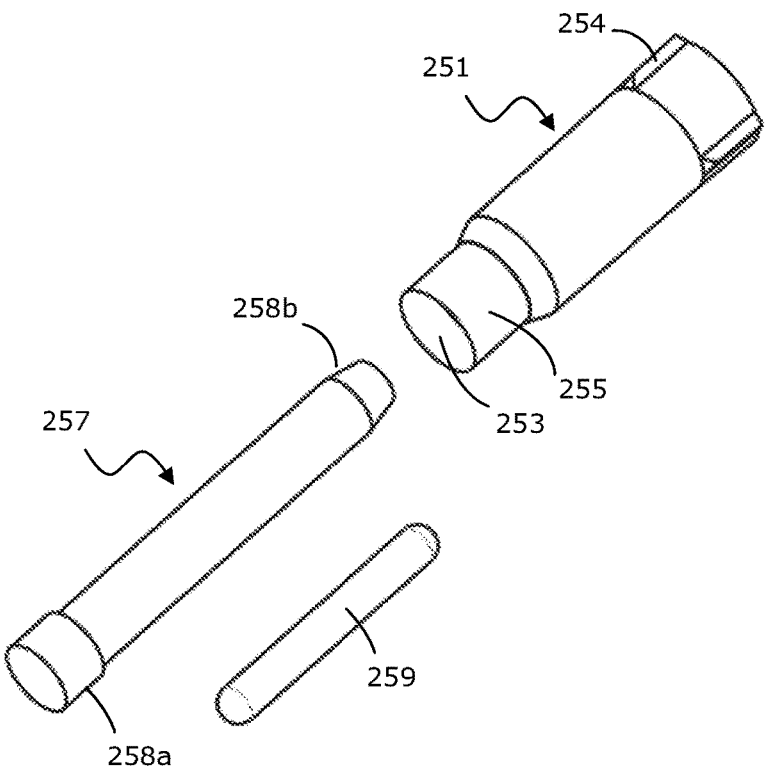
FIG. 1a is an exploded view of one form of collector.

The RFID system may be selected according to the anticipated manufacturing and use conditions of the tissue sample collector. For example typical passive tag, active reader systems operating in the low frequency range can provide robust identification devices suitable for embedding in molded plastic components at a unit cost that is appropriate to the present purpose. The tag 259 illustrated in FIGS. 1a and 1c is typical of the form of RFID tags of this type.

However other systems, such as a passive tag system operating in the UHF range can provide lower unit costs. Tags of this type are available that are claimed to be sufficiently robust for embedding in molded plastic components.

In very small sizes suitable for the present application, these UHF tags may have very small read range. However this does not pose a particular problem as the RFID reader 122 may usefully be integrated into the tissue sampler, or mountable to the tissue sampler, immediately adjacent the position that a sample collector occupies at the time of use. For example a tag may be integrated alongside the magazine at location 121a in FIG. 1c. There may be multiple readers 122 on one tissue sampler. E.g. a reader at the front of the tissue sampler to read a tag on an animal, operator or magazine to be inserted into the tissue sampler. Another reader may be located adjacent the magazine as described above and as shown in FIG. 5a.

Figure 5:
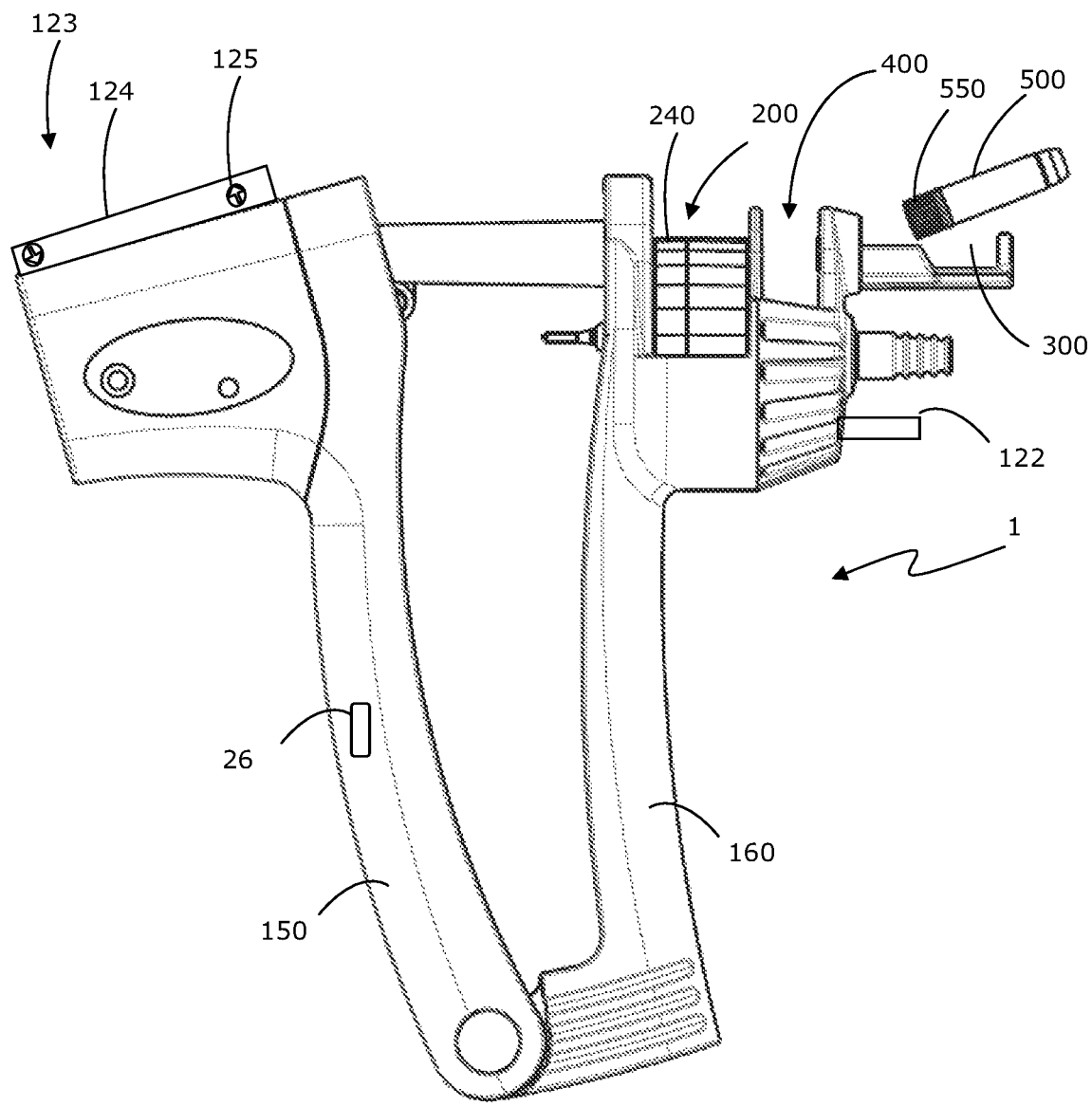
FIG. 5 is a side view of one form of tissue sampler in which a storage container is about to be placed into the tissue sampler.
Figure 5A:
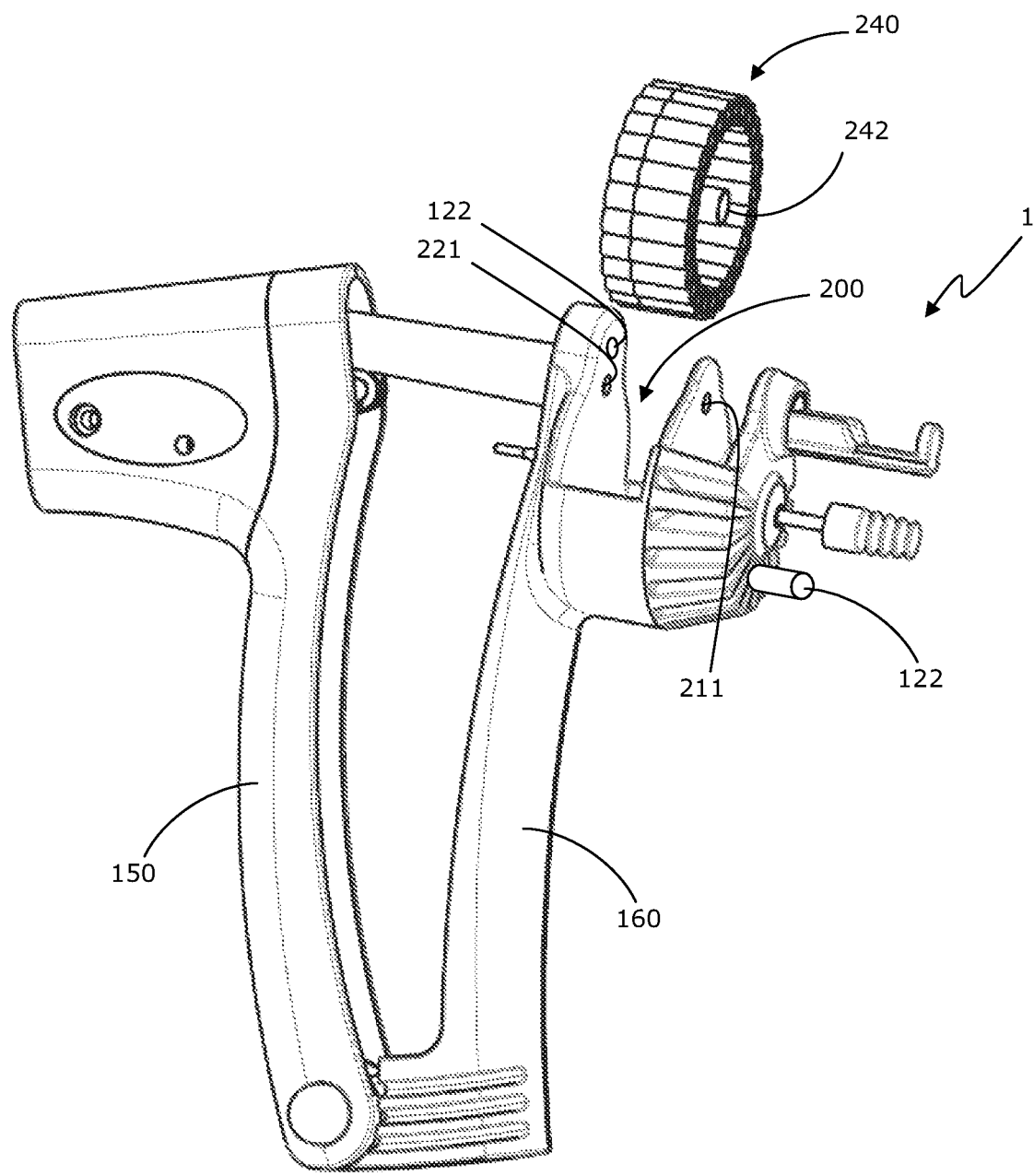
FIG. 5a is a perspective view of the tissue sampler with a collecting device magazine about to be placed into the magazine housing of the tissue sampler.
Figure 6:
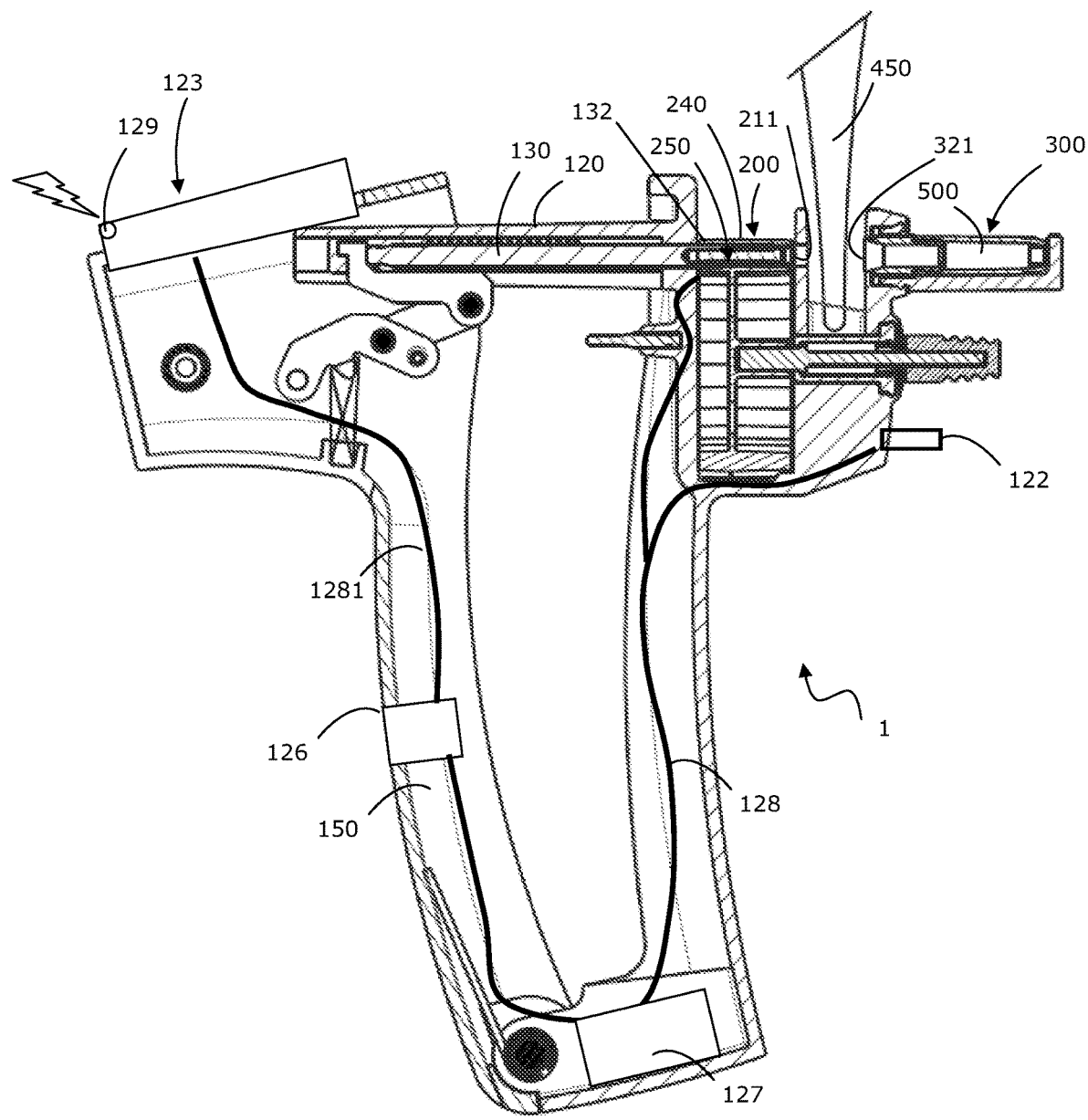
FIG. 6 is a cross-sectional side view of the tissue sampler of FIG. 5 in which an animal's ear is located in the cutting region.
Figure 6A:
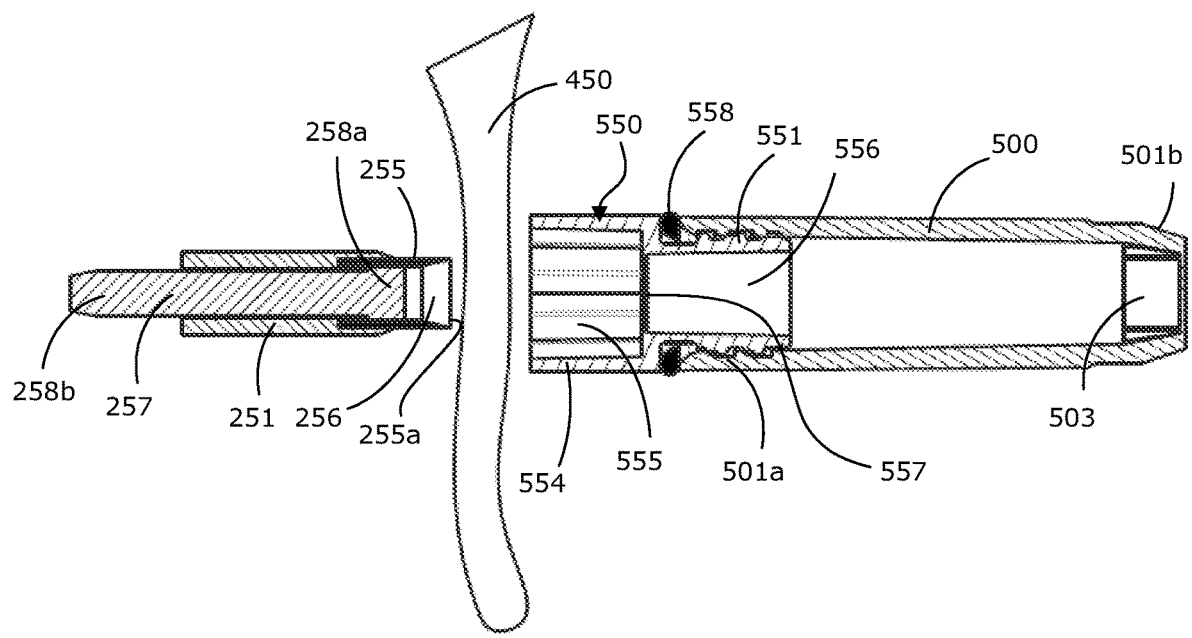
FIG. 6a is a cross-sectional side view of one form of collector before taking a tissue sample from an animal's ear and placing it into a storage container.
Figure 6B:
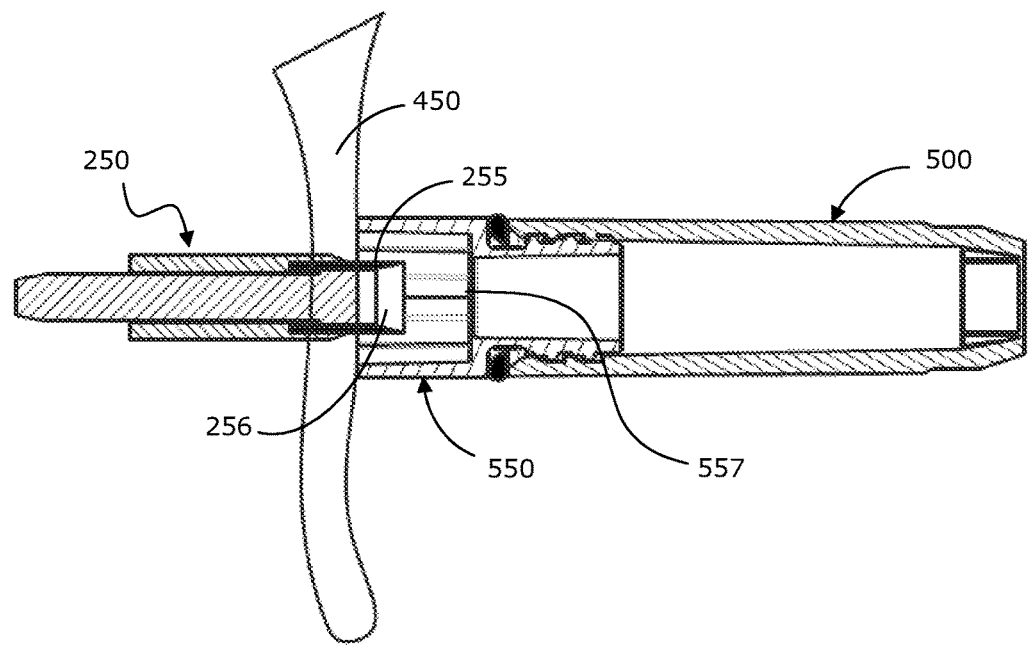
FIG. 6b is a cross-sectional side view of the collector of FIG. 6a when cutting a tissue sample from the animal's ear.
Figure 6C:
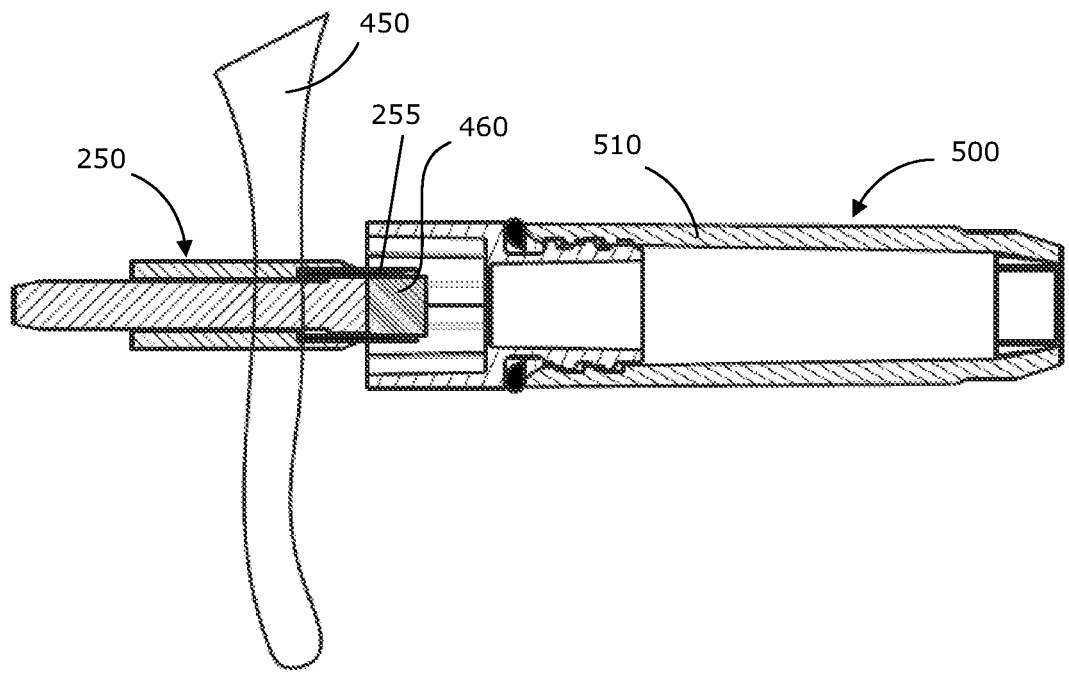
FIG. 6c is a cross-sectional side view of the collector of FIG. 6a after a tissue sample has been cut.
Figure 6D:
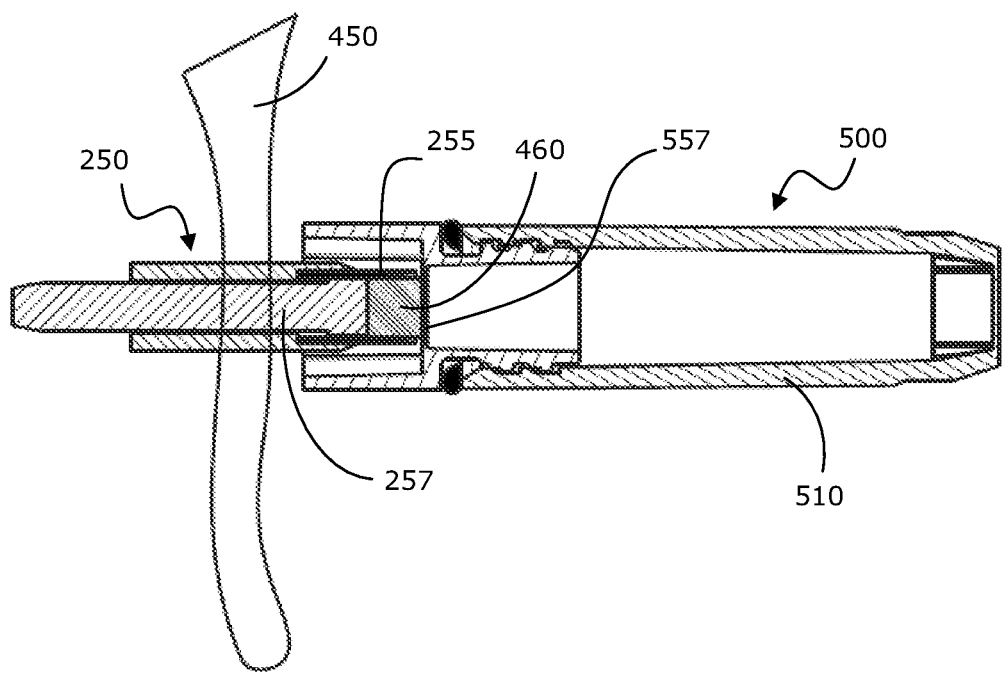
FIG. 6d is a cross-sectional side view of the collector of FIG. 6a pressing against a membrane in the cap of the storage container.
Figure 6E:
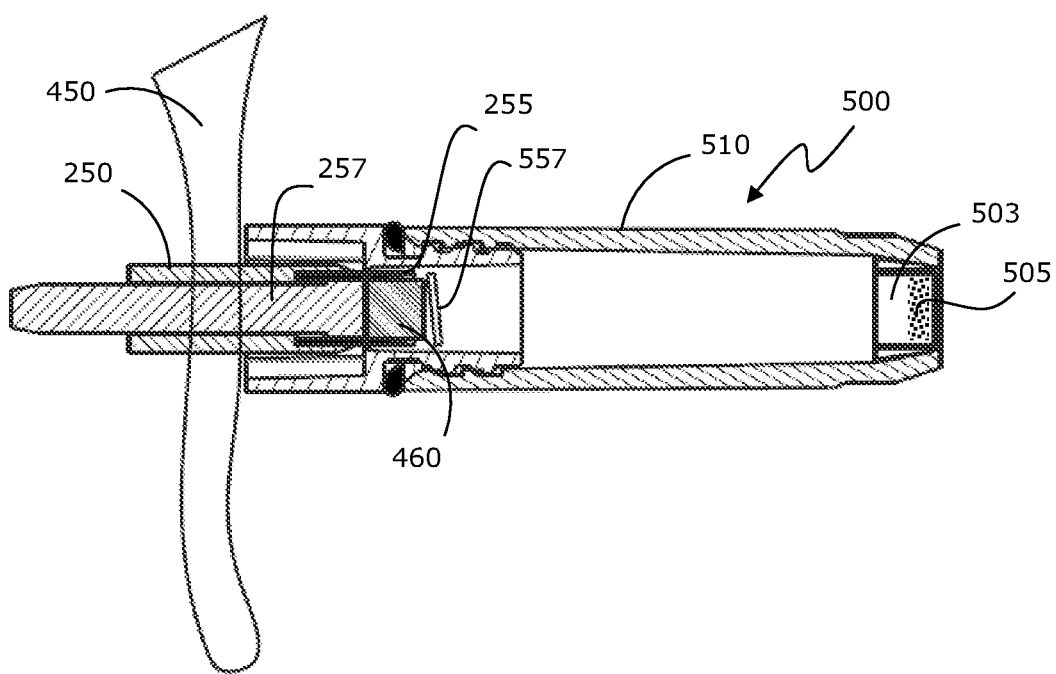
FIG. 6e is a cross-sectional side view of the collector of FIG. 6a after the membrane has been broken.
Figure 7:
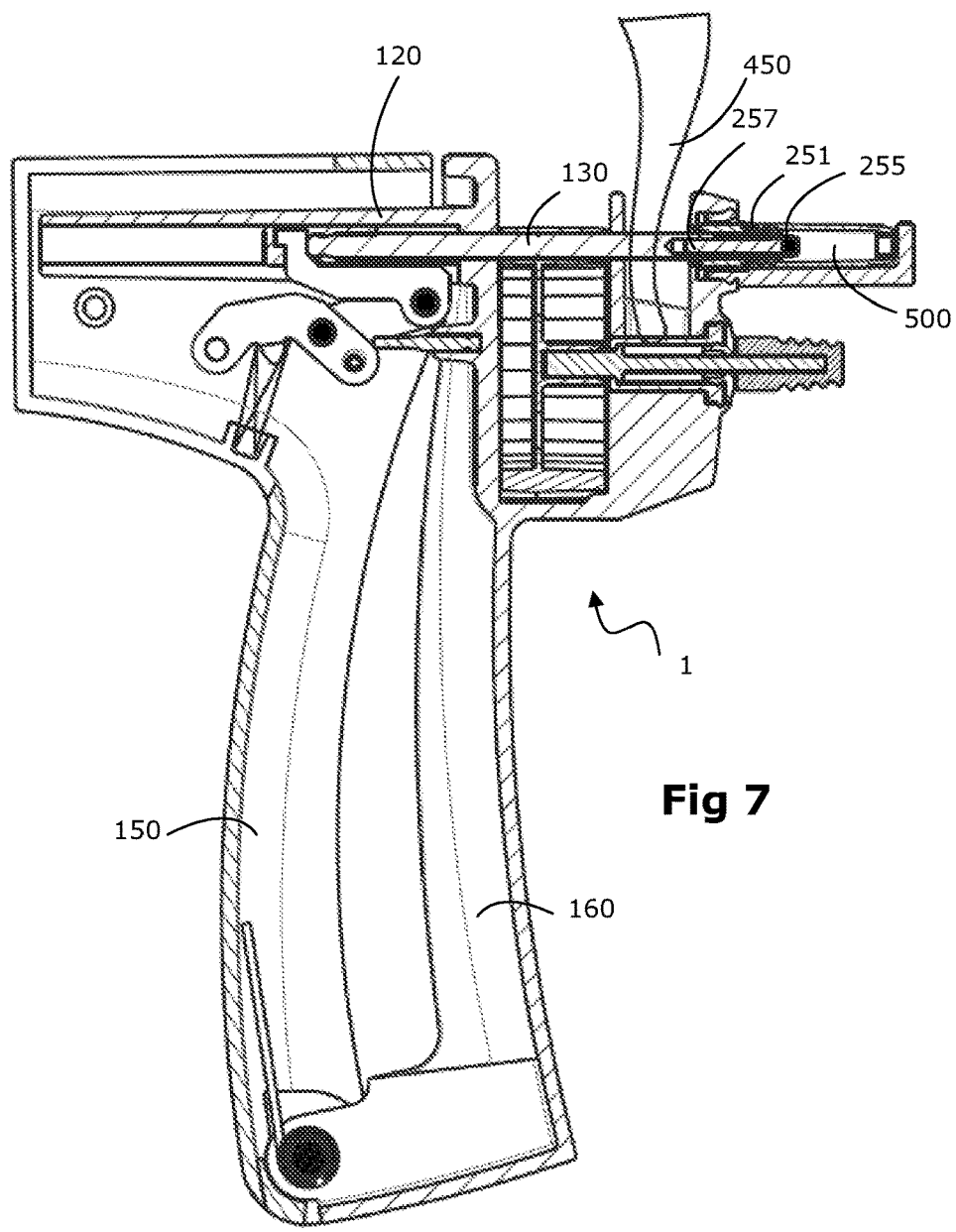
FIG. 7 is a cross-sectional side view of the tissue sampler of FIG. 6 in which a tissue sample has been cut from the animal's ear.
Figure 7A:
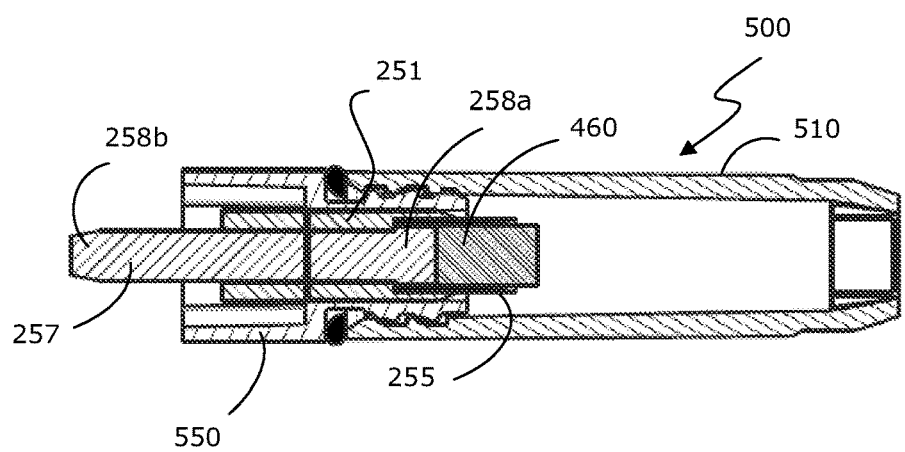
FIG. 7a is a cross-sectional side view of the collector of FIG. 6a in which it is plugging the first end of the storage container.
Figure 8:
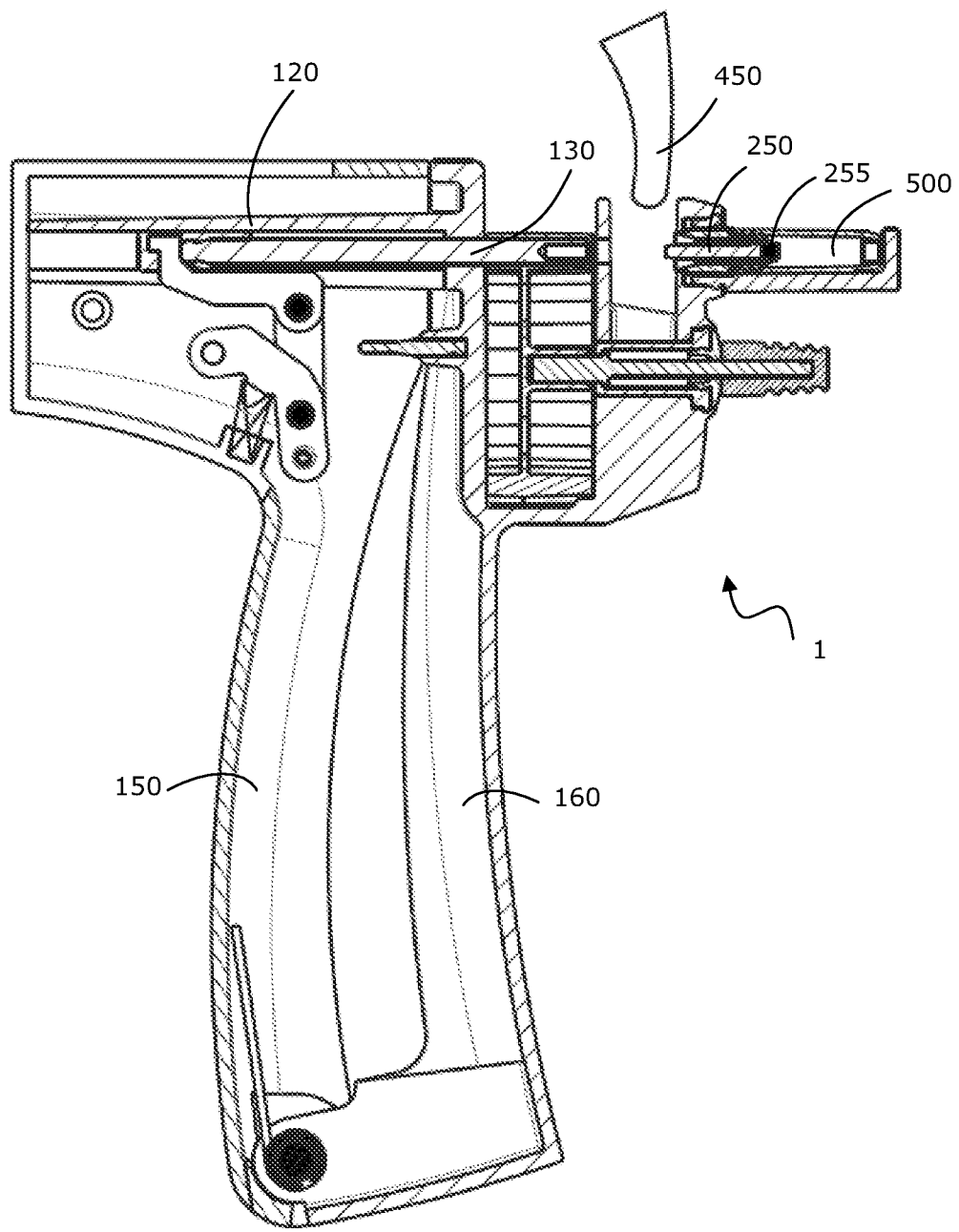
FIG. 8 is a cross-sectional side view of the tissue sampler of FIG. 6 in which the animal's ear is removed from the cutting region and the collector has plugged the storage container.

The reader may include a user interface 123, and a program configured to provide a visual or audible indication (e.g. a screen 124 as shown in FIG. 5) that it has successfully read an identity from a tag 259 in the actuation location. In this way the reader may read the identity of a tag as soon as the magazine is advanced, and the user may actuate the device at their leisure once the reader has confirmed that the identity of the tag has been read. The user interface 123 may have controls 125 to scroll through previous readings to confirm their status or allow other interactive operations. Furthermore the tissue sampler may comprise a power source to run the electronic components. The power source may be wirelessly charged or plugged in to charge. In other embodiments the squeezing or activation of the tissue sampler trigger may charge the electronic system like a dynamo. In FIG. 6, a battery 127 is shown to power the reader and associated paraphernalia.

The reader may then communicate that tag identity for recording to a database. For example the preferred reader may include data storage 126, data network capability and a program configured to transfer data either at the time of capture or after capture. Data may be stored in any suitable format, for example as a series of files, or a single file, or a database. Data storage or communication may be removable or accessible by other means such as wireless means 129 or physical connections. Communication between the reader 122, battery 127, data storage 126 and user interface 123 may wireless or via a circuit 128 as shown in FIG. 6.

The data stored in the database may include a record for the RFID identity of the sample collector together with any other collected data including, for example, one or more of a time and date, an animal identity, a tube or vial identity and an operator identity. One or more of these additional identities may also be read using a machine reader, for example from an RFID tag 259 included on the animal or on the vial or tube, or in an identity card of the operator. The other identity data may be accumulated by the reader used for reading the RFID tags of the sample collectors, or may be read by other devices. The other identity data may be stored at the same time as the identity of the sample collector, or may be stored as it is read, which may be before or after collection of the sample collector identity data.

Alternatively the reader may store tag identity data along with some other data, with the stored data to be extracted later by upload or transfer of the data storage medium. For example the data may be stored on a removable data storage device. The other data is preferably sufficient to allow the sample collector identities to be matched with identities of the animal sampled, the vial used to cap the sample, or both. For example, this other data may include one or more of the time of reading, time of actuation of the tissue sampler in relation to the identified sample collector, the order of reading or the order of actuation.

As an alternative to reading the sample collector data at the time of collection, the sample collector identity data may be read after collection of the sample, for example in conjunction with reading a storage vial identity from the storage vial. Later reading has the disadvantage that it allows more opportunity for discrepancy by less closely linking in time the identity of the animal and the identity of the sample.

The sample collector identity data may be stored with other identity data prior to taking the sample, for example where the collector is supplied in conjunction with one or more of an allocated vial or animal ID tag. In that case the stored record may be established in advance, and the collection protocol may require that the user check the identity of the animal or the vial or both at the time of taking the sample. This check may be facilitated by displaying identity data for the user to check, or by making a comparison between stored data and data read from identity tags at the time of taking the sample.

The particular means of recording and storing the data may be varied without departing from the intended scope of the present invention. The present invention lies in particular in providing an EID on or in the sample collector, where the sample collector cuts the tissue sample and retains it (at least initially), so that the identity of the sample collector and the animal from which the sample has been cut may be matched in an electronic record that is known to be correct at the time the sample is taken. Preferably this electronic record also includes the identity of a vial or closure that encloses the cutting portion of the sample collector.

FIGS. 1*a* to 1*g* show a preferred form of a collector 250. The collector can be used with the tissue sampler as will herein after be described or with another suitable tissue sampler.

The collector 250 comprises a punch 251 having a body with a cutter 255 at a cutting end 252*a* of the punch 251. The punch 251 also has an opposing pushing end 252*b*. The body of the punch 251 preferably has a slot or bore 253. The bore 253 extends from one end of the punch to the other. It preferably extends along the length of the punch between the cutting end and the pushing end, as shown in FIGS. 2*a* to 2*e*. Preferably, the punch has an elongate straight body and the bore is centrally located within the body of the punch.

In one form, the outer surface of the body of the punch comprises guides in the form of one or more projections or recesses to help locate the punch within a cap of a storage container as will be described later. In the embodiment shown in FIGS. 2*a* to 2*d*, the guides comprise three evenly spaced ribs 254 that project from the pushing end 252*b* of the punch. A lead-in 254*a* may also be provided.

A cutter 255 is provided at the cutting end 252*a* of the punch to remove a sample from an organism. The cutter may be attached to the punch or it may be integral with the punch so that the cutter and punch are formed as a single part. The cutter 255 may be cylindrical. It may alternatively be of another shape suitable to remove a sample. The sample may for example be taken from the tip of the ear of an animal and the cutter may as a result be U or V shaped or other shape. It need not take a core sample but an edge sample instead. Being of a hollow section such as cylindrical does offer the added benefit of being able to retain the sample, as a plug, by the cutter. The cutter can remove a sample plug that ends up sitting in the cutter.

A free end of the cutter 255 is presented to form a cutting edge 255*a*. The cutter 255 preferably extends from and surrounds one end of the bore 253 of the punch at the cutting end of the punch body to form a projecting surrounding wall or walls. Preferably, the bore 253 of the punch is cylindrical so that the cutting edge is substantially circular. A sample holding section 256 is formed by the cutter, preferably within the projecting wall(s) of the cutter. In this way, the cutter provides a sample holding section 256 such as a bore. The bore is a blind bore terminated by the end of the plunger 257. It is aligned with the bore formed in the body of the punch. For the sake of simplicity, the bore 253 of the punch, when referred to in this specification, should be interpreted to include the bore formed in the body of the punch and the bore formed in the cutter because the two are preferably contiguous.

A plunger 257 is held at the bore 253 of the punch and forms part of the collector. In one form the plunger protrudes at least partially from the punch. In other forms it is contained entirely within the bore. Being within the bore helps protect it and prevent tampering therewith at least unless an appropriate tool is used.

The plunger preferably incorporates the RFID tag 259 as herein before described and as shown in FIGS. 1*a* to 1*d*.

The plunger has a first end 258*a* and an opposing second end 258*b*.

The plunger 257 can be seen to extend into the bore 253 of the punch 251. The fit of the plunger in the bore is snug yet allowing for the plunger to slide relative the punch. In the preferred form the plunger outer surface is contiguous the inner surface of the bore. This ensure that a seal is created there between, preventing ingress of contaminants from the pushing end of the punch to the cutting end, through the bore.

The plunger and punch are in a sliding relationship with each other whether it is using a bore and pin like relationship or other. They are in a sliding relationship so that the sample can be pushed off the cutter.

The plunger in the preferred form extends into the bore of the punch and can push a plug of sample tissue from the sample holding section 256. This pushing may be to push the sample into a storage container with which the collector becomes associated after sample taking. It may occur at the time of sampling or well after such as in the laboratory at where the sample will be processed. In the lab the sample may be pushed off the cutter and into a test tube, or into a storage container if used, for analysis.

Figure 1B:
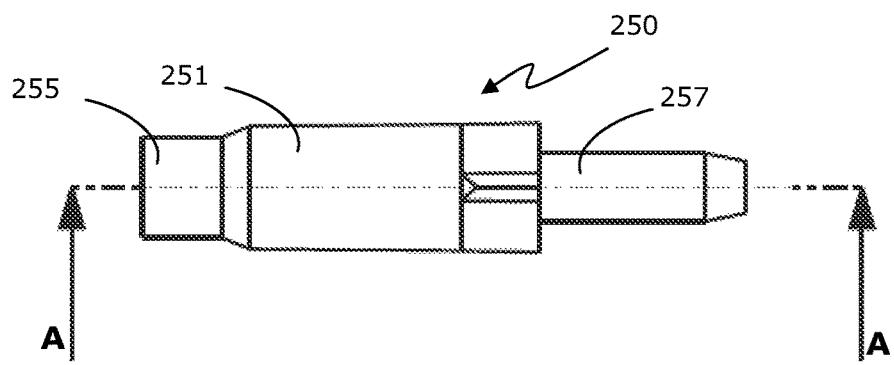
FIG. 1b is a side view of one form of the collector.
Figures 1C, 1D:
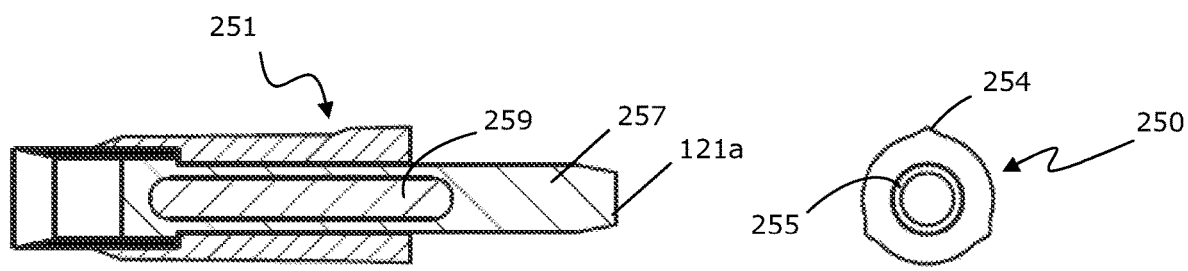
FIG. 1c is a cross-sectional side view of the collector taken along line A-A of FIG. 1b.
FIG. 1d is an end view of the collector of FIG. 1b.
Figure 1E:
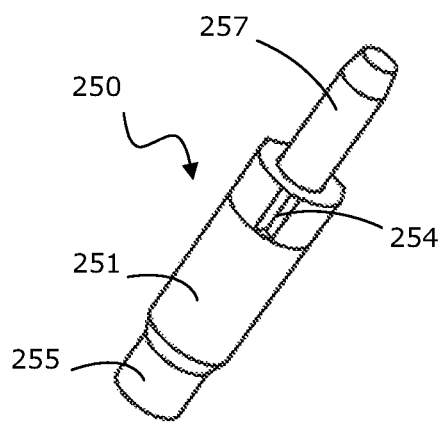
FIG. 1e is a perspective view of another form of the collector.
Figure 1F:
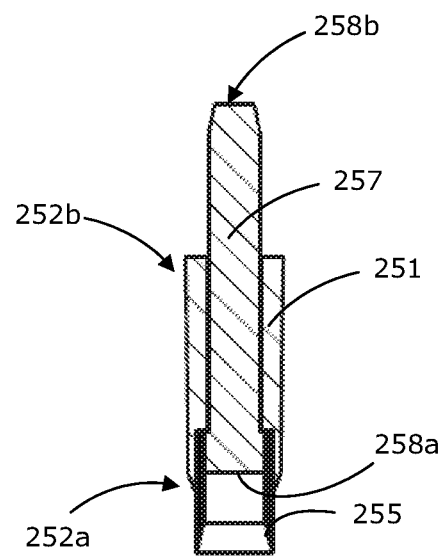
FIG. 1f is a cross-sectional side view of the collector of FIG. 1e.
Figure 1G:
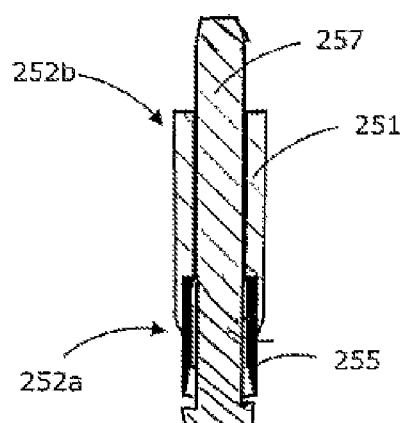
FIG. 1g is a view of the collector in a condition where the plunger is actuated.
Figure 2A:
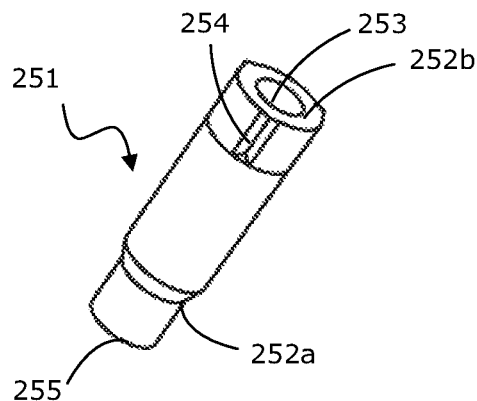
FIG. 2a is a perspective view of one form of punch for a collector
Figure 2B:
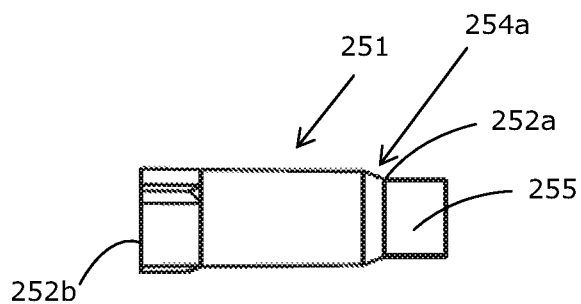
Figure 2C:
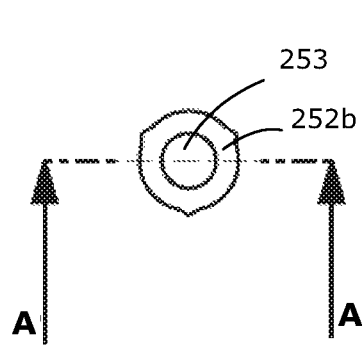
Figure 2D:
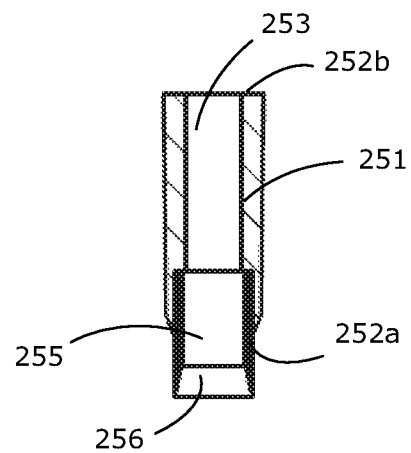
FIG. 2d is a side view of the punch taken along line A-A of FIG. 2c.
Figure 2E:
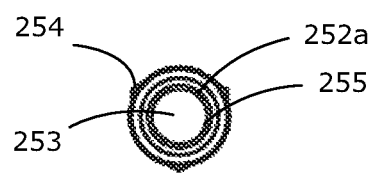
Figure 3A:
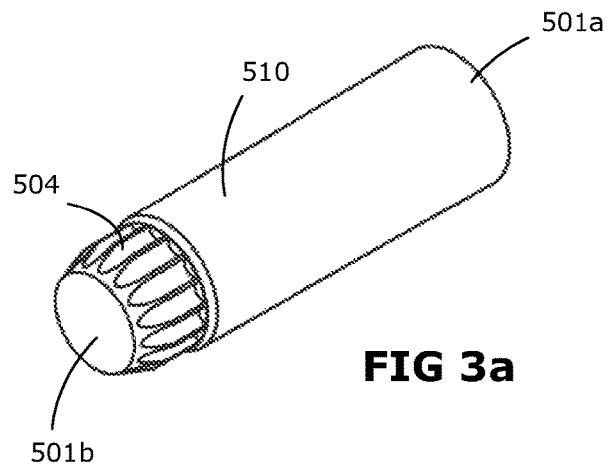
FIG. 3a is a perspective view of one form of storage body.
Figure 3B:
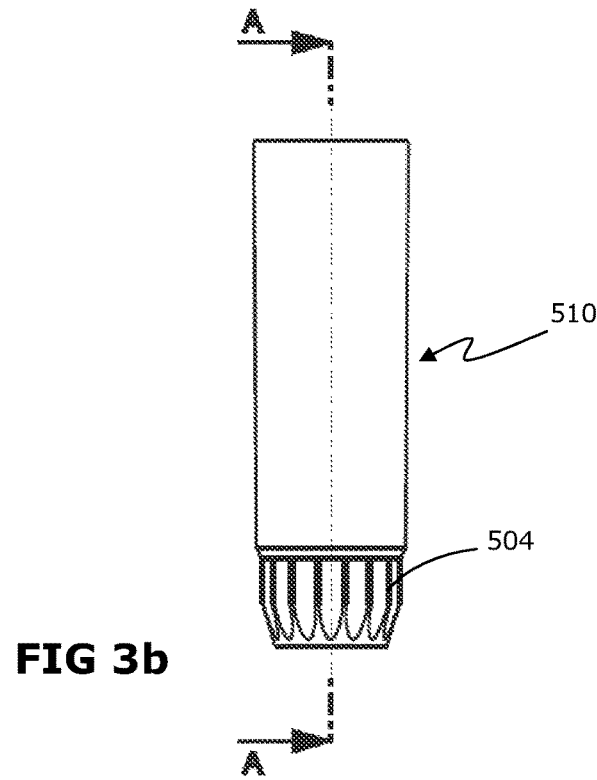
Figure 3C:
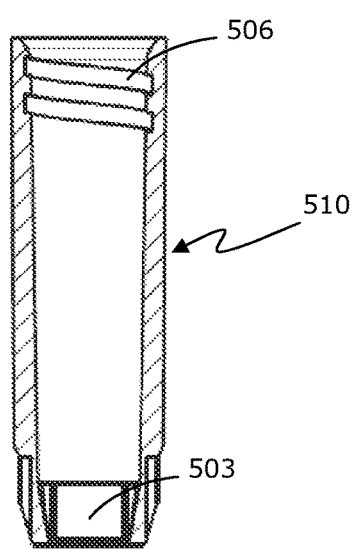
Figure 3D:
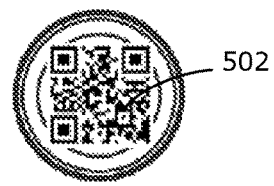
Figure 3E:
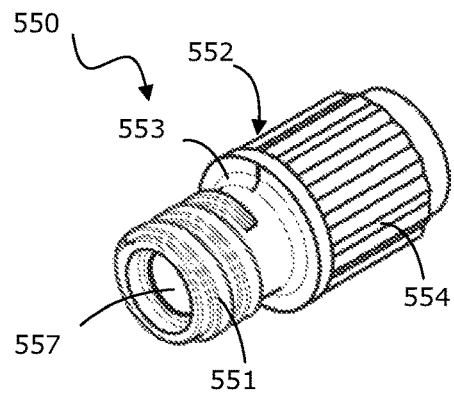
FIG. 3e is a perspective view of one form of cap for a storage container.
Figure 3F:
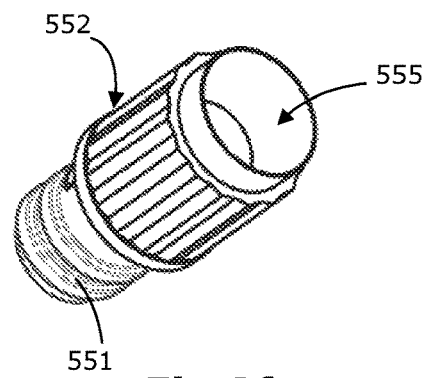
FIG. 3f is another perspective view of the cap of FIG. 3e.
Figure 3G:
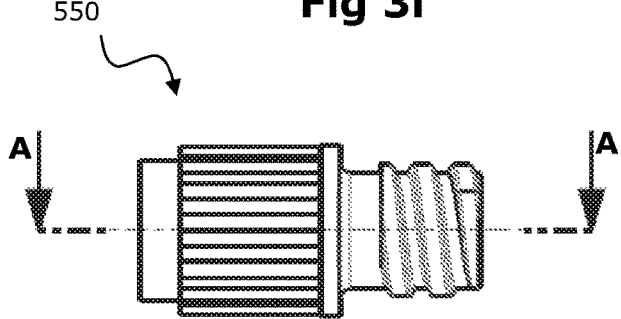
FIG. 3g is a side view of the cap of FIG. 3e.
Figure 3H:
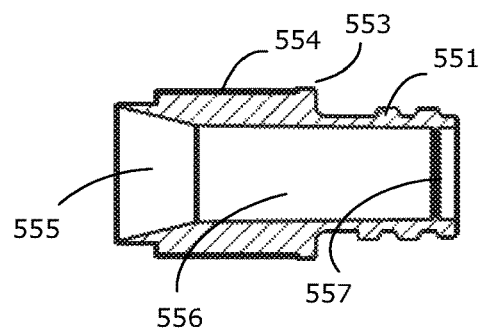
FIG. 3h is a cross-sectional side view of the cap of FIG. 3g.

The plunger is able to be positioned in an active position as shown in FIG. 1b and be moved to a plunged position as seen in FIG. 1g.

When the plunger is in an active position, ready for the collector to remove a sample from the cutter, the second end of the plunger may project from the pushing end of the punch and the first end of the plunger is held within the bore of the punch between the sample holding section and the pushing end of the punch. Preferably, at or near the first end 258a of the plunger is enlarged or provides some form that creates an interference to the removal of the plunger from the punch in one direction. A similar enlargement (not shown) may be provided at or near the other end of the plunger. The or each enlargement helps prevent the removal of the plunger that carries the RFID tag from the collector.

The collector is adapted to cut a sample of tissue from an animal or plant, using the cutter. The sample can temporarily be held by the cutter such as within the sample holding section. To release the sample from the sample holding section, the plunger can be pushed from its active position so that it moves in the direction of the sample. It may be pushed into the bore of the punch more and toward the cutting edge and through the sample holding cavity so that the tissue sample is pushed off the cutter.

Although in a preferred form the punch is substantially tubular and the plunger is substantially cylindrical, it is envisaged that the punch and plunger may be of any suitable complementary shape. For example, the bore of the punch may have a square cross-section, and the plunger may also have a square cross-section of a slightly smaller size so that the plunger can slide within the bore of the punch. It should be appreciated that the cutting edge of the cutter could also be of any suitable shape and size to cut a tissue sample that fits within the storage container for receiving the sample. For example, the cutting tip may be square, oval, star shaped or irregularly shaped.

As mentioned, the collector may be used together with a storage container. In the preferred form the collector is held by a tissue sampler as will herein after be described that also holds the storage container at the time of sampling.

In one form, as shown in FIGS. 3a to 3d, the storage container 500 comprises a container body 510 having an open first end 501a and a closed second end 501b, which forms the base of the container body, although it should be appreciated that the container body will not always be oriented so that the base is at the bottom of the container body.

Figure 9:
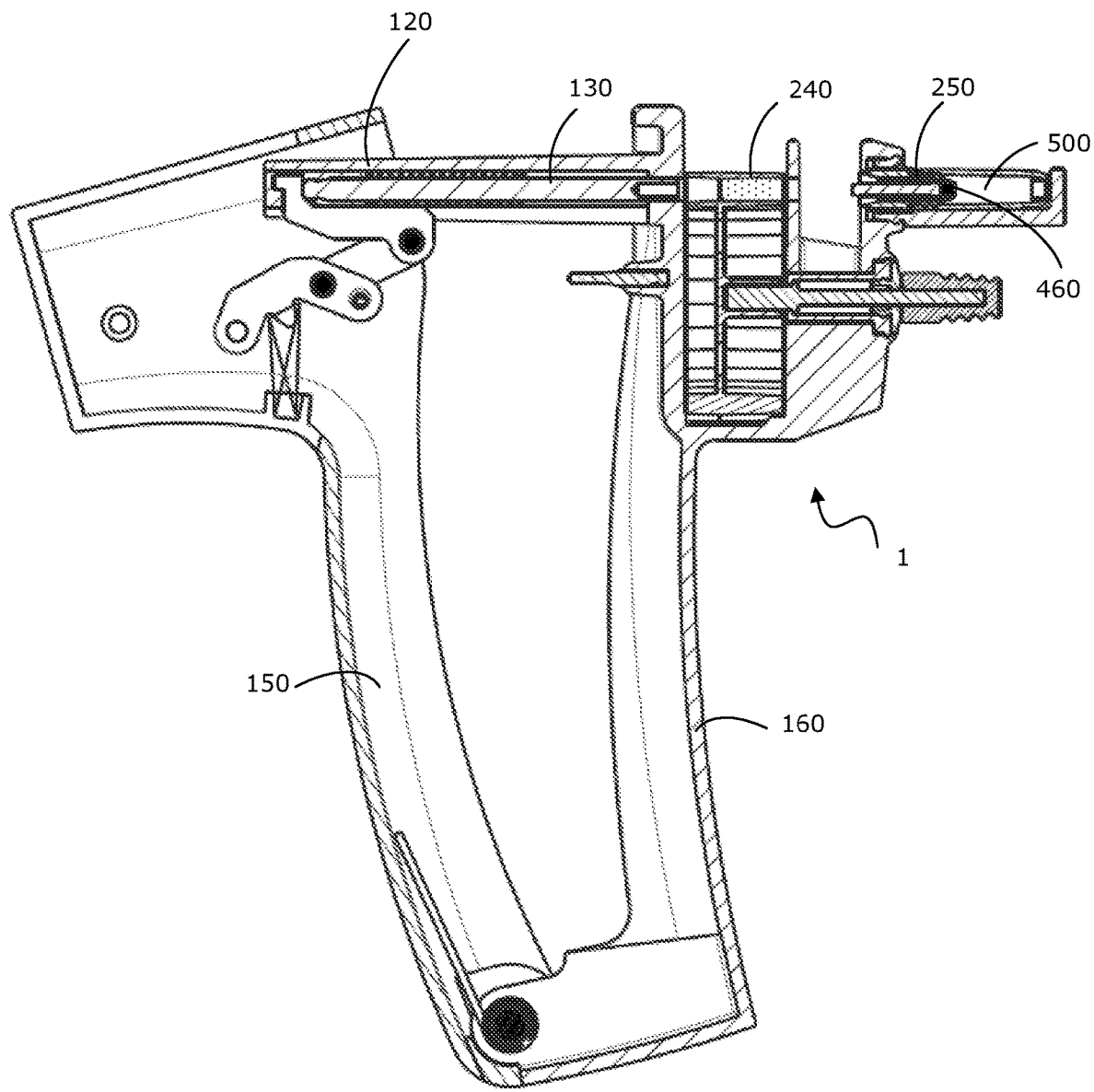
FIG. 9 is a cross-sectional side view of the tissue sampler of FIG. 6 in which the ram has been retracted through an empty chamber of the collector magazine and is returned to its rest position.
Figure 10:
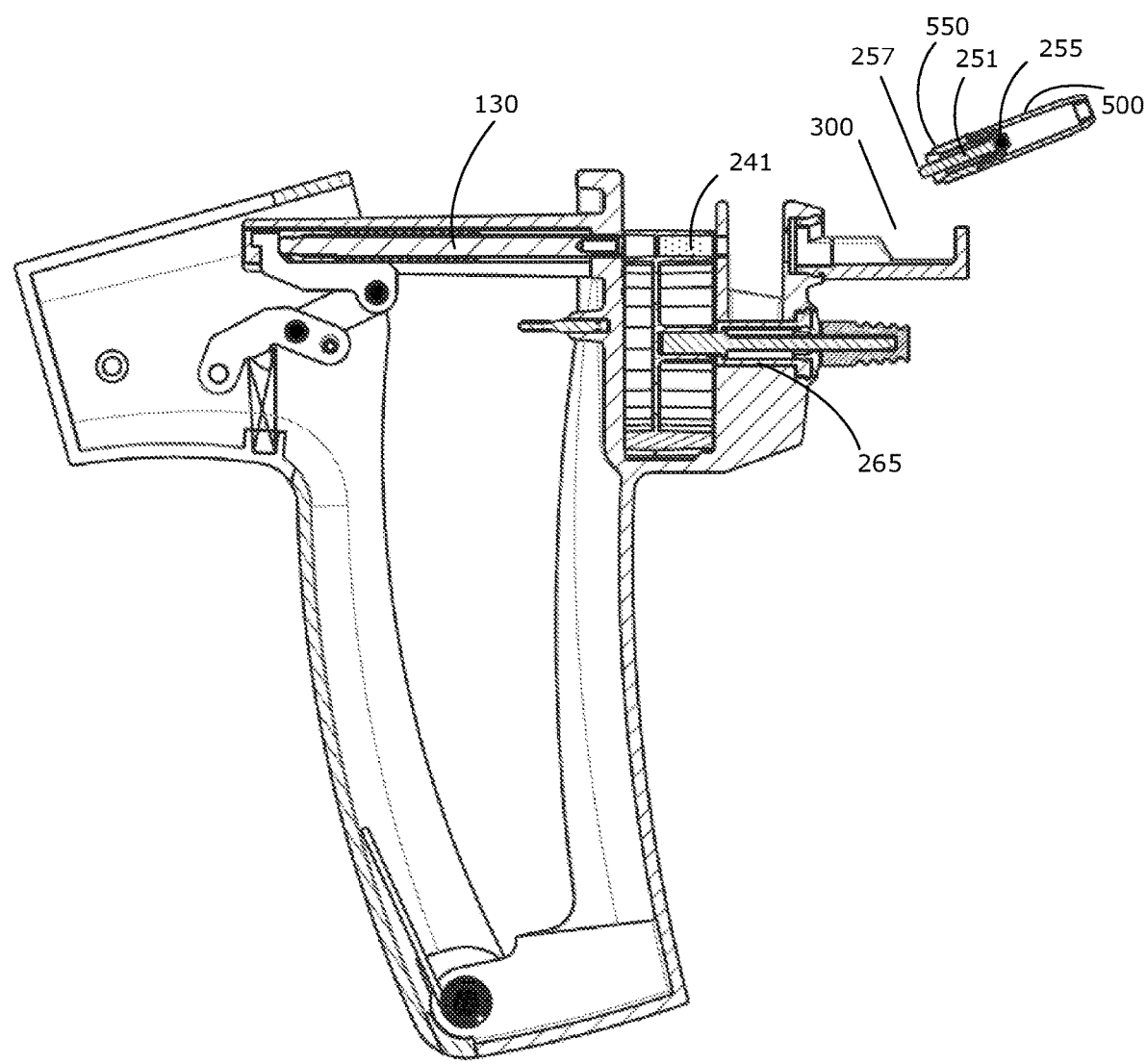
FIG. 10 is a cross-sectional side view of the tissue sampler of FIG. 6 in which the storage container containing a tissue sample and collector is being removed from the sampler.

Optionally, the base of the container body is flat and unique indicia 502, such as a bar code, QR code, matrix code, or the like machine readable code is provided on the base, as shown in FIG. 9d. Alternatively or additionally, unique indicia is provided along the side of the container body. The unique indicia is used to provide information about the source of the sample that will ultimately be placed within the storage container 500. An RFID tag may instead or also be attached to the container.

In one form, the container body 510 comprises a tissue sample chamber 503 at its base to receive a tissue sample. A preservative 505 may be provided in the tissue chamber.

Preferably, the outer surface of the container body comprises anti-rotation means 504 located at or near the base of the container, as shown in FIGS. 3a to 3d. The anti-rotation means comprise one or more recesses and/or projections adapted to prevent the container body from rotating within a cell of a holding rack, as will be described later in this specification.

Optionally, the storage container comprises a cap that attaches to the open first end of the container body to seal the container body. Alternatively, the cap may have an aperture/passage formed therein through which a tissue sample can pass to be placed in the container body. In this form, the cap is attached to the container body, but does not fully seal the container body. The storage container, preferably at the cap, provides a die for the punch to cooperate with in cutting the sample away from the animal. The die includes the aperture/passage. This allows a shear action like removal of the tissue by the die/punch combination.

Preferably, the container body comprises a threaded region at or near its first end that meshes with a threaded region of the cap to allow the cap to be screwed onto and off the storage container. Alternatively, the cap is attached to the open end of the container body with a snug fit. In yet another form, the cap comprises a lip on its inner surface that nests within a channel that surrounds the outer surface of the container body near the open end of the container body. As will be appreciated, the cap may be attached to the container body in any other suitable arrangement and these are just some examples that could be used. A threaded relationship is preferred because it assists in cap removal.

In one form the storage container 500 comprises a cap 550 that is screwed onto a threaded region 506 of the container body 510, as described above. In particular, the cap comprises a threaded shaft 551 that is adapted to engage with a threaded interior region 506 of the storage container 500 so that a first end of the shaft projects toward the base 501b of the container. Alternatively, the shaft may have a threaded bore that is adapted to engage with a threaded exterior region of the container body so that a first end of the shaft projects toward the end of the container body. A collar 552 extends from the opposing second end of the threaded shaft. The collar 552 comprises an outwardly projecting annular flange 553 and a guide wall 554 that extends from the periphery of the flange 553 in a direction away from the shaft 551 to form a substantially cylindrical wall. Preferably, an outer surface of the guide wall is contoured or textured to provide a knurled cap.

A centrally located recess 555 is provided within the collar 552 and between the guide wall. The recess may be specially shaped for engagement with a correspondingly shaped cap-release tool to remove the cap from the container body. For example, the recess 555 may have a tool-engageable edge 559 that provides the recess with a cruciform shape, star shape, hex shape, square shape, oval shape, or any other regular or irregular shape that corresponds to the shape of a tool for inserting into the recess and turning the cap to unscrew the cap from the container body. However, it is preferred that the outer surface of the guide wall is shaped to correspond with the shape of a tool, or to at least provide a gripping region, for gripping the outer wall and turning the cap to decap the storage container.

The recess 555 aligns with a passage 556 that is centrally located through the cap. The cap also comprises a breakable seal 557, which may be in the form of a membrane, or the like, that extends laterally across the cap. The seal may be formed integrally with the collar and shaft of the cap so that the entire cap is made as one part. Preferably, the seal is located at or near a first end of the shaft, but in other forms, the seal may be located within the collar of the cap or in any other suitable location. The seal 557 may be of any suitable material, such as polypropylene, rubber, polyethylene, or the like. When the cap 550 is attached to the body of a container body 510 so that the first end of the shaft projects into the body, the seal 557 extends across the body to seal the first end 501a of the container body. Preferably, the cap 550 also comprises a second seal 558, such as an o-ring, that fits over the outside of the threaded shaft 551 and abuts the collar 552 of the cap. In this form, when the cap is attached to the body of a storage container, the second seal is positioned between the first end 501a of the body and the collar 552 of the cap 550 to seal the connection between the cap and the body. In this arrangement, the cap can be screwed onto a sterile body to hermetically seal the containment region in the body. The body interior can remain sterile until the seal is broken and a tissue sample is placed in the container body.

In the preferred form the cap and the container body are engaged to each other in some tamper evident manner. This allow for detection of the removal of the cap from the container body. Preferably the tamper evident manner provides some visual evidence of tampering. For example, connecting tabs may be provided between the collar and an attachment ring of the cap that is securely attached to the container body. In this form, if the cap is twisted away from the attachment ring (such as by unscrewing the cap from the body), the connecting tabs break to indicate that the storage container has been tampered with. A shrink wrap over the container cap interface may be used as a tamper evident indicator. A sticker may be used that will pull apart when the cap and container are separated. A frangible ring or the like could be used also.

Figure 4:
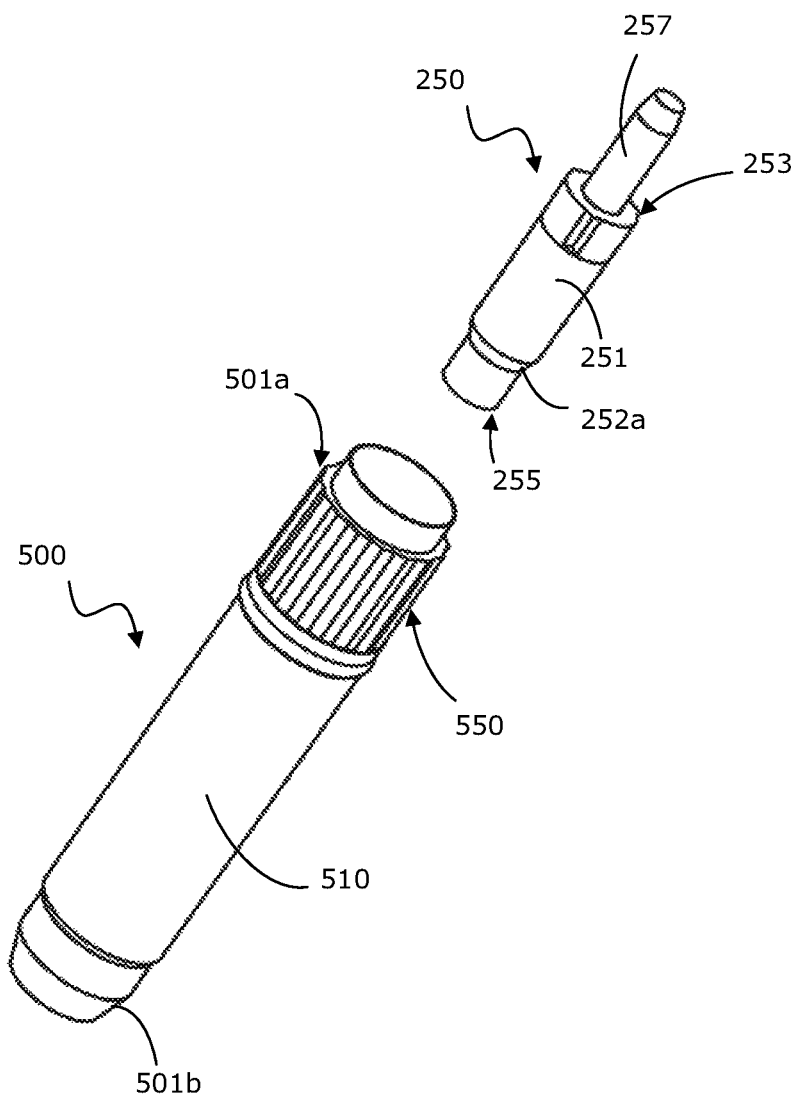
FIG. 4 is a perspective view of one form of the collector before being inserted into a storage container.

The storage container, when used, and collector are aligned at the time of sampling as shown in FIG. 4. They are separated prior to sampling so that part of the organism from which the sample is to be removed can be located there between.

As will now be described, the collector and when used the storage container may be so held for sampling purposes by a sampler. The sampler is described in our co-pending international application PCT/NZ2014/000106 which by way of cross reference is hereby incorporated. Pneumatically or electrically operated samplers or other are also envisaged as being adaptable for use with the present invention.

The storage container is dimensioned to fit within the storage container holder 300 of the tissue sampler 1 as shown in FIGS. 5 and 6 and to receive a collector through the first end of the storage container, as indicated in FIG. 4.

When a tissue sample is to be taken, a storage container 500 is placed in the container holder 300 so that its first end 501 faces toward the cutting region 400, as shown in FIG. 5.

A plurality of collectors 250 may be positioned within a magazine housing 200 loaded into the tissue sampler. The magazine can sequentially present each collector for sampling. This is achieved by aligning the collectors individually with an actuator such as a ram 130 of the sampler 1.

Figure 11:
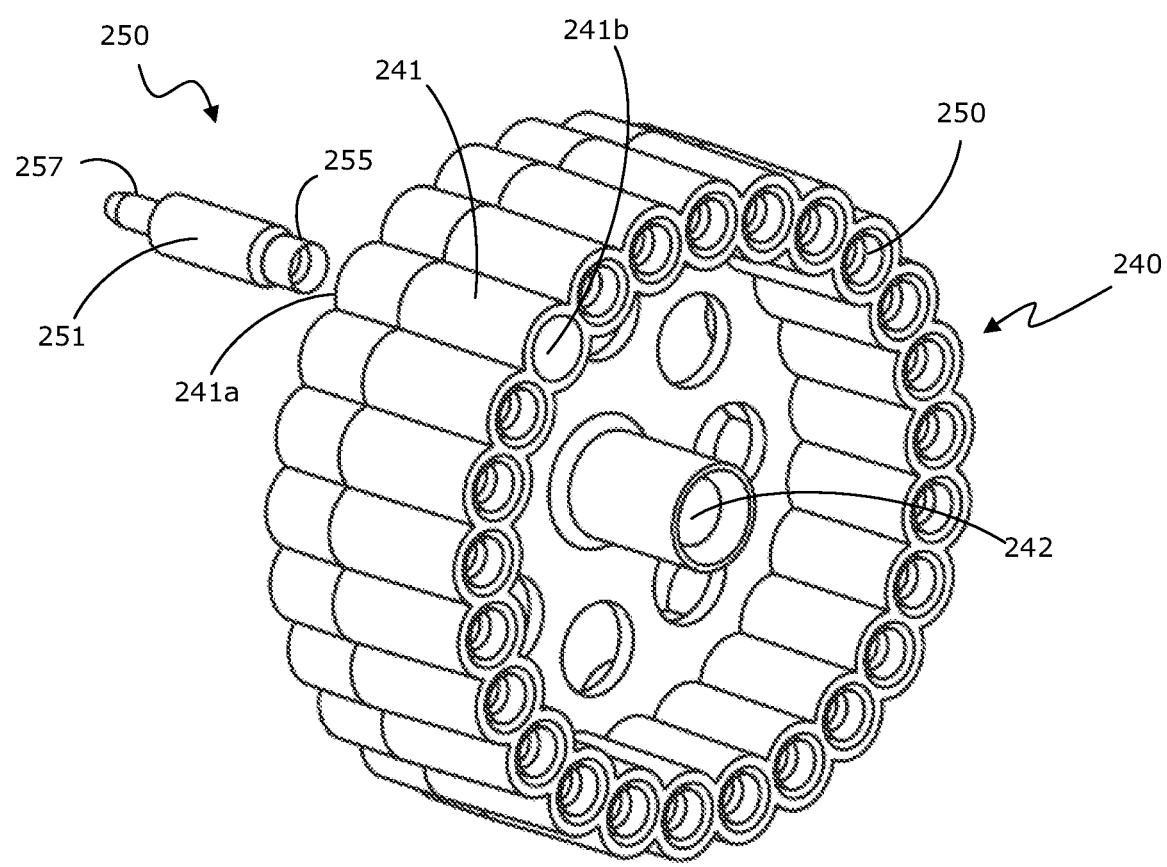
FIG. 11 is a perspective view of a collecting device magazine.

As shown in FIG. 11, the magazine housing 200 is sized to receive a magazine 240 comprising a plurality of chambers 241, each chamber being adapted to hold a collector 250 therein and having open first and second opposing ends 241a, 241b. The magazine, is preferably in the form of a cylinder having a centrally located axle or bore 242 that extends through or into the magazine. The chambers are positioned concentrically around the bore and preferably near the circumference of the magazine. Preferably, at least a portion of the chambers in the magazine 240 is of a transparent material, so that the presence of a collector in any of the chambers can be identified. In the embodiment shown in FIG. 11, the magazine comprises 25 chambers, although the magazine may have any suitable number of chambers. The magazine may carry an RFID or barcode or other machine removable code. In the preferred form the magazine can rotate to index collectors for actuation. In other forms the magazine may translate instead.

The second end of the collector aligns the ram 130 and the cutting edge 255a of the cutter 255 aligns with a cutting region aperture 211 of the sampler, as shown in FIG. 6.

The storage container holder 300 of the tissue sampler is adapted to hold a storage container 500 therein.

As shown in FIG. 5 the cutting region 400 comprises a space in which tissue 450 from a sample specimen can be positioned. In FIG. 6, an animal's ear 450 is schematically shown positioned within the cutting region. The ear, or other item, is kept in the cutting region as a tissue sample is cut from the ear.

A ram 130 is positioned within the ram housing 120 of the sampler. The ram forms part of an actuating means, which also comprises a trigger 150 operably connected to the ram 130. A guiding recess 132 is formed in the first end of the ram and is shaped to correspond with the second end 258b of the plunger, which projects from the punch. The guiding recess 132 is dimensioned so that the projecting portion of the plunger can fit within the recess and so that the first end of the ram 121a can abut the pushing end 252b of the punch. This prevents the ram actuating the plunger during sampling, only driving the collector through the sample specimen by pushing on the punch.

The ram 130 is adapted to slide back and forth within the ram housing 120 as the trigger 150 is engaged and disengaged.

To cut a tissue sample, a user may use the sampler as herein described. They may insert a storage container 500 into the holder 300 so that a portion of the storage container is pushed into the sampler receiving aperture 321 so that the first end of the storage container projects slightly from the sample receiving aperture 321 and into the cutting region, as shown in FIG. 6. The magazine 240 is orientated so that the cutting edge of a punch 251 of the active collecting device 250 is aligned with the cutting region aperture 211 and the second end of the plunger 257 is aligned with the ram receiving aperture 221. As will be appreciated, the magazine can be placed into the tissue sampler before or after the storage container is placed in the tissue sampler.

The user then holds the handle of the tissue sampler and positions the sampler so that tissue 450 to be sampled (such as of an animal's ear) is located in the cutting region 400, as shown in FIG. 6. The user squeezes the trigger 150 toward the gripping member 160 to move the trigger from the disengaged position to the engaged position.

The ram moves through the ram receiving aperture and pushes against an active collecting device. The ram continues pushing to push the collector out of the chamber of the magazine, through the cutting region aperture, into the cutting region, and toward the storage container.

As the ram pushes the collector through the cutting region, the cutting end of the punch pushes the animal's ear (or other tissue) against the first end of the storage cap and the first wall of the cutting region. The cutting edge of the punch is then pushed through the ear or other tissue to cut a sample plug from the tissue.

The tissue sample is held within the sample holding region of the collector and the collector is pushed into the first end of the storage container to place the sample within the container.

As shown where the first end of the storage container 500 comprises a cap 550 with a seal 557 as described above, the collector 250 is pushed into the recess 555 formed in the cap. Optionally, the wall of the recess comprises one or more ribs for engaging with the guiding ribs 254 of the punch to guide the body of the punch within the cap. As the collector pushes into the cap, the cutting edge 255a of the punch presses against and then pierces the seal or membrane 557 to form an opening to the storage body. The cutting end of the punch (holding the plunger therein) is then pushed through the opening so that the sample holding region 256, and the sample 460 held within the cavity 256, is located within the body of the storage container 500. The collector fills the opening formed by the broken seal to close off the first end of the container. In particular, the diameter of the punch is sized to fit snugly within the opening formed in the cap so that the cap is able to hold the collector therein. Preferably, the second end of the plunger projects from the pushing end of the punch and the first end of the plunger is located within the bore of the punch between the sample holding cavity and the pushing end of the punch. In this arrangement, the plunger can be depressed and pushed through the sample holding region to release the tissue sample into the storage container. This may occur manually or by tool and may be done at sampling or after.

When the collector closes off the first end of the storage container, the punch and the plunger are held by the cap of the storage container so that the cutter is held within the container body. It is therefore not necessary for the user to handle the punch with its sharp cutting edge or to otherwise remove and discard the punch from the tissue sampler.

The trigger mechanism of the sampler 1 is such that the action of cutting the tissue sample, placing the sample in the storage container, and releasing the animal's ear is almost instantaneous so that if the animal reacts to having its ear cut and pulls away, there is little chance that the animal can pull the tissue sampler from the user's hand before the ear is released.

The storage container, including the cap holding the collector can then be removed from the container holder and an unused replacement storage container can then be fitted into the holder. The collector magazine is rotated incrementally until the next chamber containing an unused collector is aligned with the ram receiving aperture and cutting region aperture, ready for another tissue sample to be taken.

Once all the collectors in the magazine have been used the magazine can be removed from the sampler 1.

Figure 12:
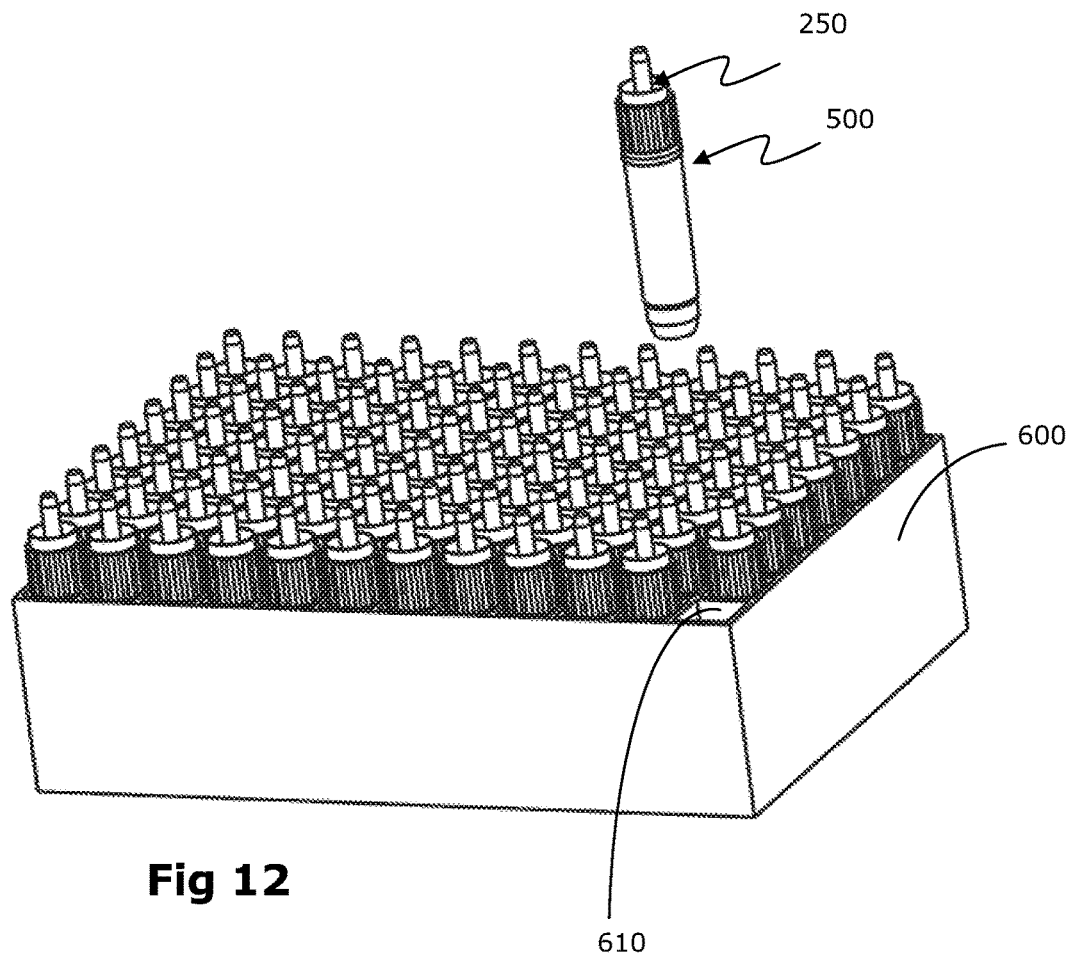
FIG. 12 is a perspective view of a plurality of collectors held within a multi-cell rack.

Preferably, the storage containers removed from the tissue sampler are placed within respective cells 610 of a multi-cell rack 600, such as a 96 well rack as shown in FIG. 12, before being sent to a laboratory for decapping and future analysis of the samples.

The collector is adapted so that the plunger can be pushed to release the tissue sample from the sample holding region and into the tissue chamber at the bottom of the container. In particular, the second end of the plunger can be depressed toward the pushing end of the punch to cause the first end of the plunger to push a tissue sample out of the sample holding region and into the body of the storage container. To assist with the release of the tissue sample, the first end of the plunger may be enlarged and may comprise an anti-stick surface formed of a non-stick material, such as Teflon™. The plunger may be depressed and pushed towards the sample holding region after the container has been removed from a tissue sampler.

Preferably, the tissue sample is held at the sample holding region when the storage container is removed from the tissue sampler. The storage containers may then be placed within respective cells of a multi-cell rack so that the base of each storage containers is at the bottom of the respective cell and the caps of the storage containers project above the cells, as shown in FIG. 12. The diameter or width of the cells is sized to be commensurate with the diameter or width of the storage containers.

Figure 13:
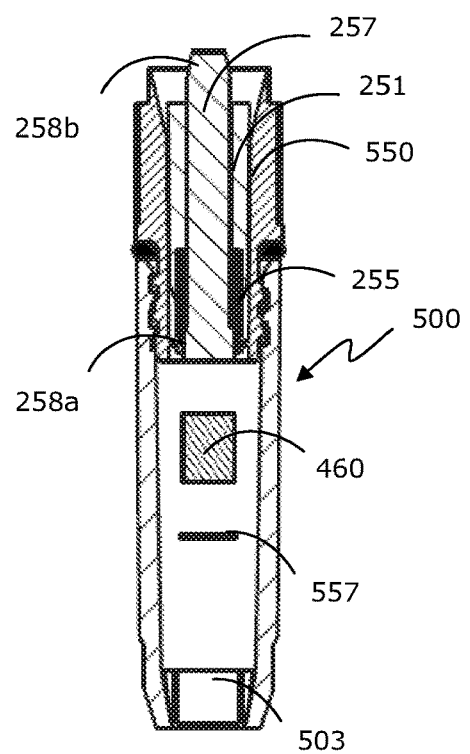
FIG. 13 is a cross-sectional side view of the storage container in which the tissue sample has been released from the collector.
Figure 14:
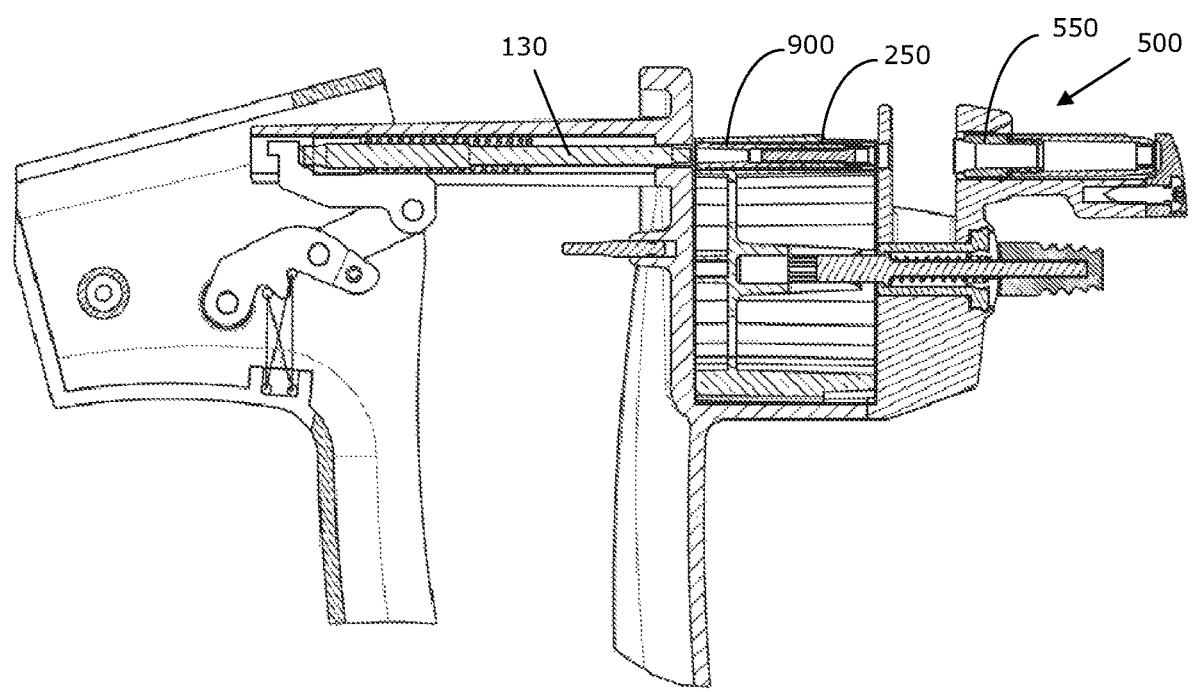
FIG. 14 is a partial cross sectional view of a sampler holding a magazine with a collector shown in the ready position aligned to a collection container and wherein a shield 900 is provided as an extension to the collector for the purposes of shielding the ram 130 from the surface or surfaces of the tissue to be sampled and thereby avoid cross contamination between samples.
Figure 15A:
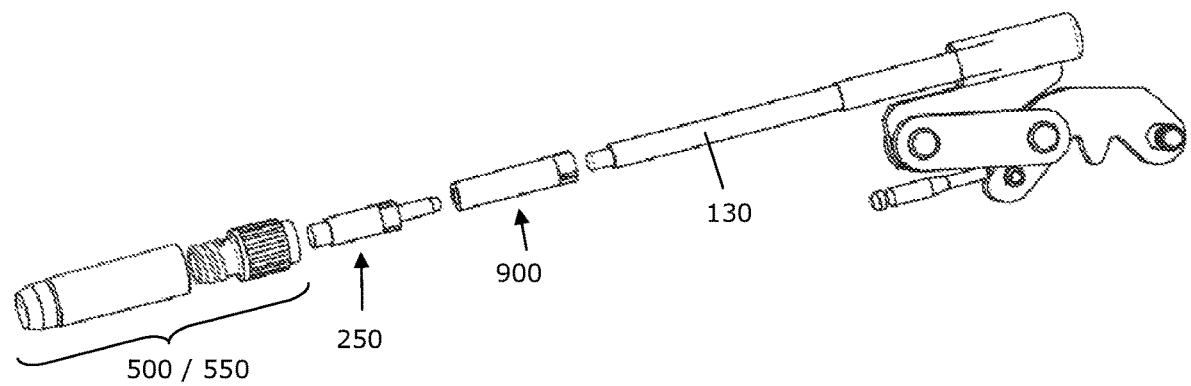
FIG. 15a is an exploded perspective view of part of the mechanism of the sampler as well as the shield 900, its associated collector 250 and the collection container.
Figure 15B:
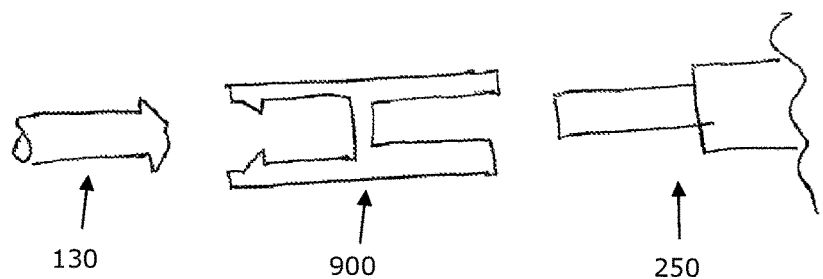
FIG. 15b is a partial sectional view of the ram 130, the shield 900 and the collector 250 and showing an arrangement between the ram and the shield to allow for the shield to be withdrawn back into the magazine after the ram having delivered the collector into engagement with the storage container to thereby attract a shield into the magazine for subsequent disposal.

A machine may be used to depress the plungers within the caps of the storage containers automatically, either by depressing the plunger consecutively or by simultaneously depressing the plungers of all n the rack. As each plunger is depressed and pushed deeper into or through the bore of the punch and through the sample holding region toward the base of the storage containers, the sample is pushed from of the sample holding region and is deposited into the chamber at the bottom of the storage containers, as shown in FIG. 13. The tool so used in the lab does not contact the sample.

Where the outer surface of the body of each storage containers comprises anti-rotation means, the storage containers are located within the respective cells of the holder so that the anti-rotation means engage with corresponding anti-rotation means provided within the cells. For example, one or more projections formed on a container body will engage with one or more recesses formed in the walls of the respective cell. The anti-rotation means of the storage containers and cells prevent the containers from rotating within the cells so that the storage containers can be automatically decapped by unscrewing the caps from the body.

To decap the storage containers, a cap engaging tool (not shown) engages with the correspondingly shaped recess of the cap, or to grip onto the outer surface of the guide wall of the cap, and is rotated in the appropriate direction to unscrew the cap from the body. Typically, a machine is provided in which multiple cap engaging tools engage with the caps of multiple containers in a rack to decap the containers of the rack simultaneously. Decapping enables the samples within the containers to be accessed and removed from the container body for analysis.

Optionally, each cell within the rack comprises an open or transparent bottom for reading unique indicia located on the base of each storage containers held within the rack so that the source of each sample can be identified and linked with the data obtained from the sample.

Laboratory testing of the sample may occur in the storage container itself is one is used, or alternatively the sample is removed from the container before testing.

Figure 16:
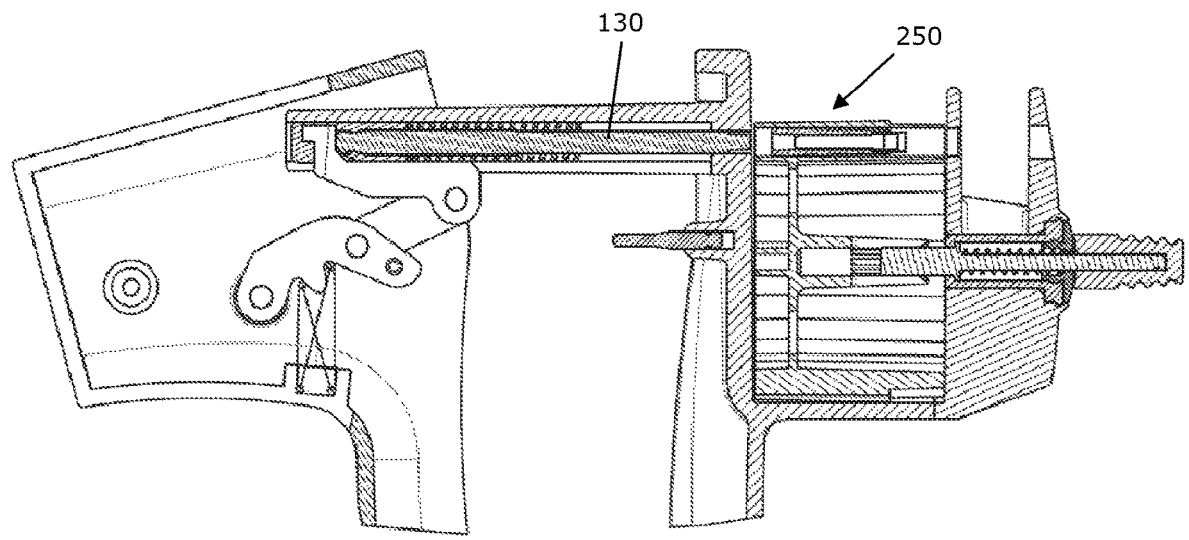
FIG. 16 is a partial sectional view for a sampler showing a collector and arranged for the purposes of retracting the collector back into the magazine after sampling, where the ram is in the withdrawn position.
Figure 17:
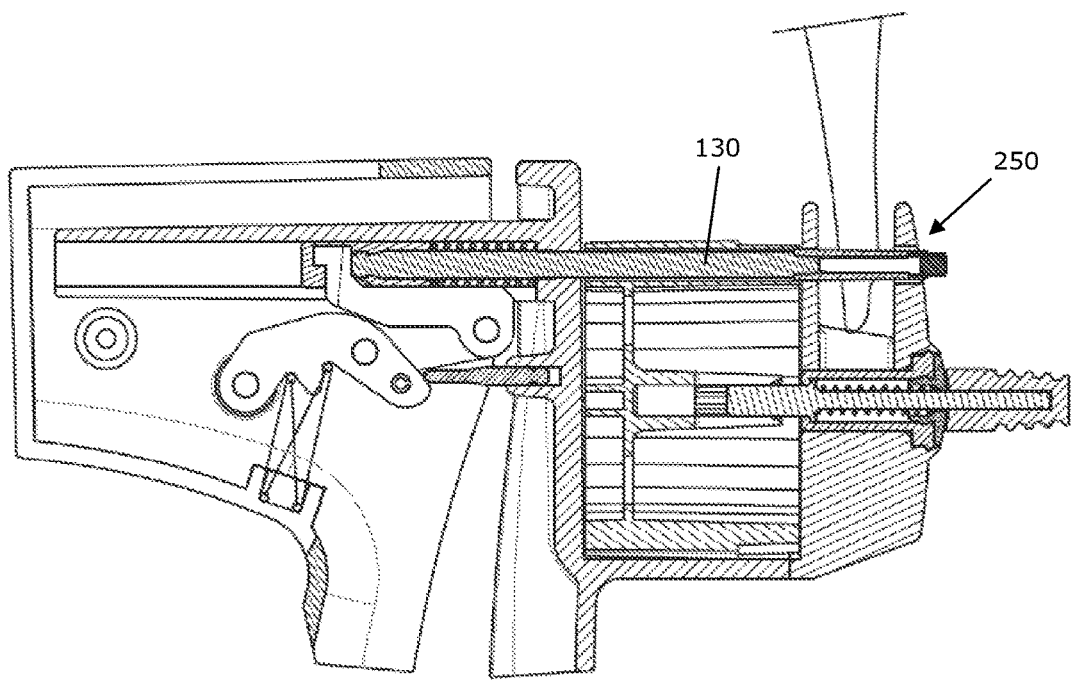
FIG. 17 shows the sampler of FIG. 16 wherein the ram has moved to the advanced position to drive a collector at least partially through the tissue to be sampled and ready to be withdrawn back into the magazine.
Figure 18:
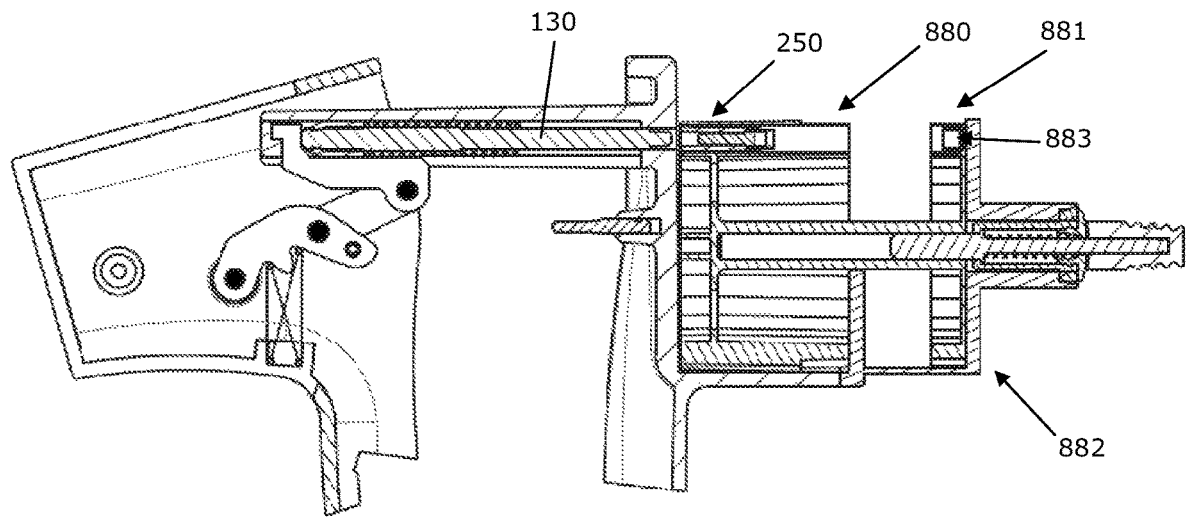
FIG. 18 is a variation of a sampler of the kind which will withdraw the collector back into the magazine wherein a secondary magazine is provided on the opposite side to the cutting region, the secondary magazine provided for the purposes of presenting a clean or fresh surface for each of the cutters of a collector to react against to avoid cross contamination, the secondary magazine optionally also carrying a plug or cap to plug or cap the sample when the ram is in a fully advanced position and for that cap to be retracted back into the magazine with the respective collector for storage.
Figure 19:
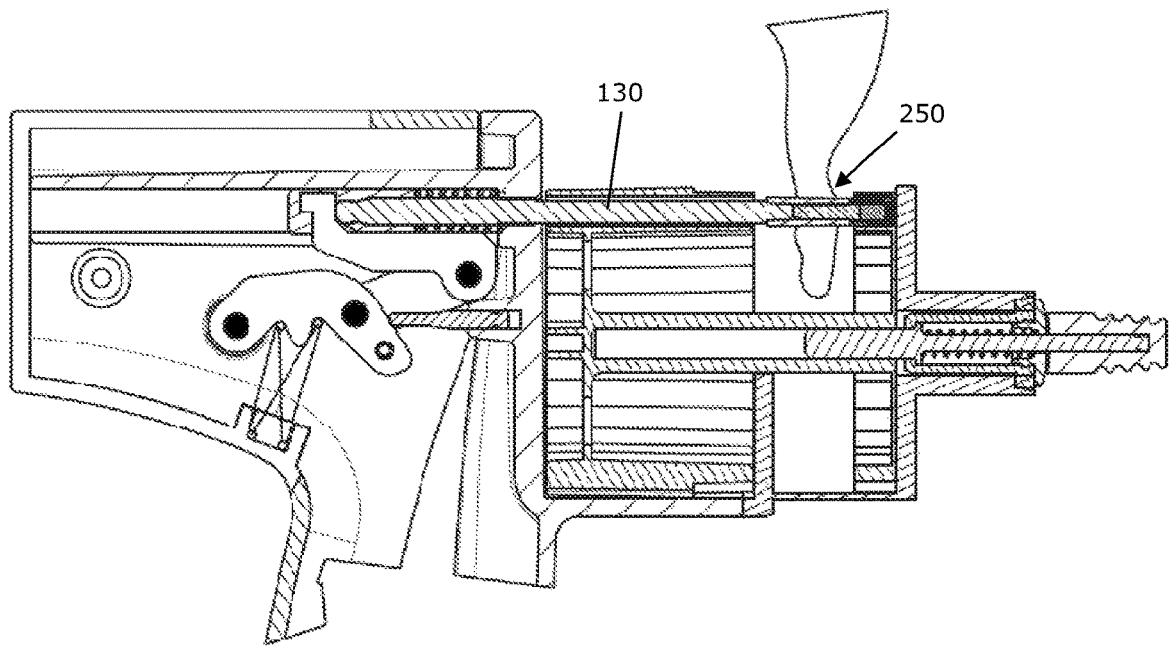
FIG. 19 shows the sampler of FIG. 18 where the ram is extended.

A variation of the present invention may not involve a storage container at the time of sampling. Instead the sample is taken by the collector by driving the cutter through the sample and then taking the sample carrying collector to a laboratory for testing. The sample containing collector, after taking a sample may be retracted back into the magazine for storage therein. This is for example shown with reference to FIGS. 16 and 17. A tapered or wedging or catch like relationship between the ram and the collector can be established to withdraw. A stop can be employed to stop the sample retaining collector in the magazine allowing the ram to then separate.

The collectors may be transported for testing without a storage container and may be housed by the magazine and the samples may be directly dispensed by depressing each plunger whilst remaining retained to said magazine, in the laboratory.

If no storage container is used, the plunger may eject the sample from the punch for subsequent testing.

A collector located RFID tag is useful for tracking and tamper prevention purposes. The RFID may be used at the time the sample is taken, it identifies the sample to a collector ID.

Prior, during or immediately after the sample is taken, the sample collector RFID tag can be read and stored along with a unique ID that is derived from a storage container ID and/or derived from an animal associated ID such as from an ear tag carried by the animal tested. This will ensure that at least 2 and preferably three individual identifiers (eg numbers) are locked to a sample taken. One from the collector RFID tag, and one from said animal associated ID and preferably from said container. These linked numbers are stored at sampling time in a database. The aim is to make it tamper resistant and limit the options to substitute samples. The container's (when used and when carrying an ID) and the collector's ID may be read during the lab processing and again checked to the database. The methods to read/transfer information from the container, collectors and ear tags at sampling would be existing technologies of reader and an intended reader within the sampler if possible. The data collected at the laboratory from the RFID devices would be unique identifier with which information derived from sample testing can be associated.

The magazine of sample retaining collectors can be capped after removal from the sampler, and sent to the lab. The lab can process the samples direct from the magazine into lab tubes, (after the samples are pushed off the punch by the plunger). The RFID tag of the collector can be matched or transferred or recorded relative a lab system number for the lab tube that the sample is deposited in. This can give flexibility if larger processing tubes are required. The sample can be ejected (by the plunger) into any required type and size of lab tube with a laboratory processing number and match that to the database numbers for the animal and original collector.

The invention claimed is:

1. A combination of an assembly for tissue sampling and an associated tissue sampler tool, the assembly comprising a sample collector and a storage container,
said sample collector being arranged to take and hold a biopsy sample from an organism upon being driven into the organism, the sample collector comprising a punch that includes a cutter with a cutting edge formed at a cutting end of the punch to remove and retain said biopsy sample, and a unique identifier on or in the sample collector, the unique identifier being machine readable at a time of use of the sample collector to take the biopsy sample,
wherein the unique identifier comprises a sample collector EID embedded in the punch, said storage container comprising a storage container body having an opening closed by a removable cap together defining a containment region, the removable cap including a passage into said containment region, and the removable cap is removably secured to the storage container body, wherein the storage container comprises a storage container unique indicia, and wherein the removable cap, in use, is sealed by said sample collector and the punch, the sample collector holding said biopsy sample in said containment region, and
wherein the associated tissue sampler tool cooperates with the assembly of the sample collector and the storage container, the associated tissue sampler tool comprising an EID reader and an EID read information storage device, wherein the sample collector EID or the storage container unique indicia, and an ID associated with the organism from which the biopsy sample is taken, are read and stored by the EID reader and the EID read information storage device, respectively, at the time of use of the sample collector taking the biopsy sample.

2. The combination as claimed in claim 1, wherein said sample collector includes a plunger mounted to the punch, said plunger being actuable to eject the biopsy sample from the punch, the sample collector EID being embedded in the plunger.

3. The combination as claimed in claim 1, including features to engage with a vial or cover, to close in the biopsy sample.

4. The combination as claimed in claim 1, wherein the storage container comprises the unique identifier.

5. The combination as claimed in claim 1, wherein said opening and said passage act as a die cooperating with said cutter to remove said biopsy sample.

6. The combination as claimed in claim 1, having been assembled by a sampler tool, the sampler tool comprising a body able to hold said sample collector and said storage container and carrying a ram to drive the sample collector from (a) a primed position, separated from said storage container by a part of the organism from which the biopsy sample is to be cut, through said part of said organism to (b) a second position where said sample collector has been driven through said part of said organism by said ram, to remove the biopsy sample from said organism, the second position lodging said sample collector at said passage with said storage container body.

7. A set of assemblies of sample collectors and storage containers, wherein each of the assemblies of sample collectors and storage containers includes the combination of claim 1, wherein each sample collector is adapted to take and hold a biopsy sample from an organism upon being driven into the organism; the sample collectors of the set all being identical except in respect of the unique identifier.

8. The set of assemblies of sample collectors as claimed in claim 7 including a plunger mounted to the punch, actuable to eject the sample from the punch, the sample collector EID being embedded in the plunger.

9. A tissue sampler tool to cooperate with the assembly of the sample collector and the storage container as claimed in claim 1, the tissue sampler tool comprising a body carrying a ram to drive the sample collector of the assembly and able to be actuated to move along a path relative the body between a first position aligned to drive the sample collector of the assembly from a primed position and push the cutter through part of the organism and a second position where said cutter has been so pushed through by said ram, to remove the biopsy sample from said organism.

10. The tissue sampler tool as claimed in claim 9, wherein the tissue sampler tool includes a magazine receptacle, to hold a magazine containing a plurality of said sample collectors, the magazine receptacle allowing the magazine to move relative the tissue sampler tool so that each of the plurality of said sample collectors can be presented for being driven by said ram.

11. A method of taking samples via a combination of an assembly for tissue sampling and an associated tissue sampler tool, the assembly including a sample collector and a storage container, said storage container comprising a container body having an opening closed by a removable cap together defining a containment region, the removable cap removably secured to the container body and including a passage into the containment region, wherein the storage container comprises a storage container unique identifier, the associated tissue sampler tool including an EID reader and an EID read information storage device, the method comprising:

a. presenting the sample collector to an actuation location of the associated tissue sampler tool, the sample collector being adapted to take and hold a biopsy sample from an organism upon being driven by an actuator into the organism, the sample collector comprising a punch that includes a cutter with a cutting edge formed at a cutting end of the punch to remove and retain the biopsy sample, the sample collector further comprising a unique identifier being machine readable at time of use of the sample collector to take the biopsy sample, wherein the unique identifier comprises a sample collector EID embedded in the punch;

b. at time of sampling, reading and storing the sample collector EID or the storage container unique identifier together with an ID associated with the organism from which the biopsy sample is taken via the EID reader and the EID read information device at the time of use of the sample collector taking the biopsy sample; and c. sealing the removable cap by the sample collector and the punch, the sample collector holding the biopsy sample in the containment region.

12. A method as claimed in claim 11, wherein the ID associated with the organism being read is located on or in the organism being sampled.

\* \* \* \* \*